US008008439B2

(12) United States Patent            (10) Patent No.:    US 8,008,439 B2
Tsukada et al.                                      (45) Date of Patent:       Aug. 30, 2011

(54) BIODEGRADABLE BIOPOLYMERS, METHOD FOR THEIR PREPARATION AND FUNCTIONAL MATERIALS CONSTITUTED BY THESE BIOPOLYMERS

(75) Inventors: Masuhiro Tsukada, Ibaraki-ken (JP); Takayuki Arai, Ibaraki-ken (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 145 days.

(21) Appl. No.: 12/076,745

(22) Filed: Mar. 21, 2008

(65)              Prior Publication Data

US 2008/0176960 A1      Jul. 24, 2008

Related U.S. Application Data

(63) Continuation of application No. 10/458,277, filed on Jun. 11, 2003, now abandoned.

(30)        Foreign Application Priority Data

Jun. 19, 2002     (JP) ................................. 2002-178126

(51) Int. Cl.
      *C07K 14/435*        (2006.01)
      *C08L 89/04*          (2006.01)
      *A61F 13/00*         (2006.01)
(52) U.S. Cl. ......... 530/353; 530/357; 530/415; 424/422
(58) Field of Classification Search .................. 530/353, 530/357, 415; 424/422
See application file for complete search history.

(56)              References Cited

U.S. PATENT DOCUMENTS 99,630 A     2/1870   Brewster

OTHER PUBLICATIONS

Baroni, "Determination of fibers in mixed textiles, wool and silk of the domestic silkworm: wool and tussah silk," La Seta 46(1):181-184, 1940 (in Italian).*
English translation of Baroni, "Determination of fibers in mixed textiles, wool and silk of the domestic silkworm: wool and tussah silk," La Seta 46(1):181-184, 1940.*
Encyclopedia Britannica Online, definition of "gel," http://www.britannica.com/EBchecked/topic/227894/gel, printed on Apr. 23, 2010.*
Kweon et al., "Structural and thermal characteristics of *Antheraea pernyi* silk fibroin/chitosan blend film," Polymer 42:6651-6656, 2001.*
Tsukuda et al., Physical and chemical properties of tussah silk fibroin films, J Polymer Sci: Part B: Polymer Physics 32:1407-1412, 1994.*
GenBank Record No. AAC32606, *Antheraea pernyi* Fibroin, Complete Protein Sequence, Dec. 7, 2000.
Giuliano Freddi et al., "Silk Fibroin/Cellulose Blend Films: Preparation, Structure, and Physical Properties," Journal of Applied Polymer Science, vol. 56, 1995, pp. 1537-1545.

Shigehiro Hirano et al., "The preparation and applications of functional fibres from crab shell chitin," Journal of Biotechnology, vol. 70, 1999, pp. 373-377.
Motoko Iwaoka et al., "Studies on Composite Fibers Produced from Fibroin of Wild Silkmoths and Cellulose," Journal of Inset Biotechnology and Sericology, vol. 71, 2002, pp. 157-160.
K. Y. Lee et al., "Antithrombogenicity and Surface Properties of Silk Fibroin/S-Carboxymethyl Kerateine Blend Films," Proceedings of the 9th International Wool Textile Research Conference, vol. II: Wool Structure, Protein Chemistry, Fine Animal Fibres, 1995, 8 pages.
Youngcheng Liu et al., "Blend Membrane of Regenerated Silk Fibroin, Poly(vinyl alcohol), and Peroxidase and Its Application to a Ferrocene-Mediating Hydrogen Peroxide Sensor," Journal of Applied Polymer Science, vol. 61, 1996, pp. 641-647.
Yoshiaki Matsunaga, "Change of Lattice Constants of Fibroin by Perfect Drying," Memoirs of the College of Science, Kyoto Imperial University, Series A, vol. XX, No. 4, Jul. 1937, cover and pp. 157-172.
Norihiko Minoura et al., "Physico-chemical properties of silk fibroin membrane as a biomaterial," Biomaterials, vol. 11, Aug. 1990, pp. 430-434.
Sung Jin Park et al., "Structural Changes and Their Effect on Mechanical Properties of Silk Fibroin/Chitosan Blends," Journal of Applied Polymer Science, vol. 74, 1999, pp. 2571-2575.
Xian-ming Qu et al., "Insect Immunity: Isolation and Structure of Cecropins B and D from Pupae of the Chinese Oak Silk Moth, *Anthemea pernyi*," European Journal of Biochemistry, vol. 127, Issue 1, 1982, citation and abstract only (1 page).
Xian-ming Qu et al., "Insect Immunity: Isolation and Structure of Cecropins B and D from Pupae of the Chinese Oak Silk Moth, *Anthemea pernyi*," European Journal of Biochemistry, vol. 127, Issue 1, 1982, pp. 219-224.
Hideki Shiozaki et al., "Salt-Catalyzed Addition Reaction of Epoxy Compounds with Various Silk Fibroins," Die Angewandte Makromolekulare Chemie, vol. 64, Issue 1, 1977, pp. 1-18.
Masuhiro Tsukada et al., "Structure and Compatibility of Poly(vinyl Alcohol)-Silk Fibroin (PVA/SF) Blend Films," Journal of Polymer Science: Part B: Polymer Physics, vol. 32, 1994, pp. 243-248.
Masuhiro Tsukada et al., "Physical Properties and Phase Separation Structure of *Antheraea pernyi/Bombyx mori* Silk Fibroin Blend Films," Journal of Polymer Science: Part B: Polymer Physics, vol. 32, 1994, pp. 1175-1181.
Masuhiro Tsukada et al., "Structure and Physical Properties of Epoxide-Treated Tussah Silk Fibers," Journal of Applied Polymer Science, vol. 44, 1992, pp. 2203-2211.

(Continued)

*Primary Examiner* — Rosanne Kosson
(74) *Attorney, Agent, or Firm* — Arent Fox LLP

(57)            ABSTRACT

A biodegradable biopolymer material consists of silk fibroin from domesticated silkworm; silk fibroin from wild silkworm; a composite material comprising silk fibroin from domesticated silkworm and silk fibroin from wild silkworm; or a composite material comprising either silk fibroin from domesticated silkworm or silk fibroin from wild silkworm and at least one secondary substance selected from the group consisting of cellulose, chitin, chitosan, chitosan derivatives, keratin from wool and polyvinyl alcohol. The material may be prepared by, for instance, casting an aqueous solution of domesticated silkworm silk fibroin on the surface of a substrate and then cast drying the applied solution. The biodegradable biopolymer material is effectively used as, for instance, a metal ion-adsorbing material, a sustained release substrate for a useful substance such as a medicine, a biological cell-growth substrate and a biodegradable water-absorbing material.

15 Claims, No Drawings

OTHER PUBLICATIONS

Masuhiro Tsukada et al., "Structural Changes of Silk Fibers Induced by Heat Treatment," Journal of Applied Polymer Science, vol. 45, 1992, pp. 1945-1953.

Masuhiro Tsukada et al., "Physical Properties of Silk Fibers Treated with Ethylene Glycol Diglycidyl Ether by the Pad/Batch Method," Journal of Applied Polymer Science, vol. 50, 1993, pp. 1841-1849.

Masuhiro Tsukada et al., "Physical Characteristics of Silk Fibers Modified with Dibasic Acid Anhydrides," Journal of Applied Polymer Science, vol. 51, 1994, pp. 345-352.

Guang Yang et al., "Structure and microporous formation of cellulose/silk fibroin blend membranes I. Effect of coagulants," Journal of Membrane Science, vol. 177, pp. 153-161.

* cited by examiner

BIODEGRADABLE BIOPOLYMERS, METHOD FOR THEIR PREPARATION AND FUNCTIONAL MATERIALS CONSTITUTED BY THESE BIOPOLYMERS

CROSS REFERENCE TO RELATED APPLICATIONS

This nonprovisional application is a continuation application which claims the benefit of pending U.S. patent application Ser. No. 10/458,277, filed Jun. 11, 2003, now abandoned, and claims priority of Application Number 2002-178126, filed Jun. 19, 2002, in Japan. The disclosures of the prior applications are hereby incorporated herein in their entirety by reference.

BACKGROUND OF THE INVENTION

1. Field of the Invention

The present invention relates to a biodegradable biopolymer material, which is degraded while being decomposed by the action of an enzyme. The biodegradable biopolymer material is thus converted into small molecules. The present invention also relates to a method for the preparation of the biodegradable biopolymer material, as well as a functional material containing the material, such as a metal ion-adsorbing material, a sustained release carrier for a useful substance, a biological cell-growth substrate and a biodegradable water-absorbing material.

2. Description of the Related Art

Materials consisting of organic polymers and possessing biodegradability are well known in the marketplace. In the medical field, materials have frequently been used which are biologically decomposed and degraded through the action of an enzyme to form small molecules. Materials recently put into practical use include, as typical examples, poly(oxy-acids), such as poly(lactic acid) and poly(glycolic acid) among the biodegradable organic polymers. These materials have widely been used as implanting materials to be embedded in the living bodies, materials for in vivo delivery or carriers for sustained release of medicines.

Poly(lactic acid) and poly(glycolic acid) show excellent resistance to chemicals. Poly(lactic acid) and poly(glycolic acid) are non-toxic and susceptible to hydrolysis. Accordingly, they have widely been used as materials capable of being decomposed and absorbed in vivo. Moreover, poly (glycolic acid) can be prepared as a very high molecular weight polymer and therefore, it is useful as a material, which should have excellent mechanical or dynamic characteristic properties, such as high tensile strength. Poly(lactic acid) and poly(glycolic acid) have been used as, for instance, biodegradable and bioabsorbable suture.

Moreover, in the medical field, silk sutures from domesticated silkworm have been used for surgical operations. The use of the silk fiber from domesticated silkworm as sutures for surgical operations dates back to the beginning of the eleventh century. The total volume of the sutures traded in this country is equivalent to about six billion yen a year (in 1985), 46% of which corresponds to the volume of the silk sutures. The silk fiber is excellent in, for instance, tensile strength and knot strength and can easily be sterilized. For this reason, silk fiber has favorably been used for sutures. Even when judging from the actual conditions of the use of the conventional silk sutures, the silk fiber can be sterilized easily. It never biologically decomposes in a short period of time when embedded in the living body. Further, when it is implanted in the living body, it only causes an insignificant antigen-antibody reaction, if any, with the biological tissues.

The cocoon fiber (the silk fiber) is a protein fiber produced and spun by matured larvae of silkworm. The silkworms are divided into two groups, domesticated silkworms reared in farmhouses and wild type silkworms. Silk fibroin fibers are those obtained by removing sericin as an adhesive substance, which covers the surface of the cocoon fiber, by treating the cocoon fiber with, for instance, an alkali.

The silk fibers from wild silkworm in general mean those produced and spun by, for instance, *Antheraea pernyi, Antheraea yamamai, Antheraea militta, Antheraea assama, Philosamia cynthia ricini* and *Philosamia cynthia pryeri*.

The foregoing silk suture is a non-absorbent material, which is never decomposed within a short period of time. Accordingly, it would remain in the living body after the suture. For this reason, it has been used for purposes different from those of the threads for a suture made from poly(oxy-acids), such as poly(lactic acid) and poly(glycolic acid), which are absorbed in the body and are decomposed into water and carbon dioxide within several weeks after the suture.

With respect to the foregoing metal ion-adsorbing material and sustained release carrier for useful substances consisting of the aforementioned biodegradable biopolymer, no product having satisfactory characteristic properties has been proposed yet.

As discussed above, poly(lactic acid) has been widely used as a biodegradable and bioabsorbable material. However, it suffers from the problems that the production cost thereof is too high, it is too expensive, it has high crystallizability, it is too hard, and it is inferior in the compatibility with soft tissues. Moreover, it also suffers from problems that its rate of decomposition cannot be easily controlled and that control of its biodegradability is also difficult, even if this material is chemically modified.

Further, fibrous poly(lactic acid) has a glass transition temperature similar to that of polyethylene terephthalate fiber. Accordingly, the poly(lactic acid) fibers possess mechanical properties similar to those observed for the polyethylene terephthalate fibers. However, poly(lactic acid) or the like has a crystallization velocity slower than that observed for polyethylene terephthalate and fibers of poly(lactic acid) are not sufficiently oriented or satisfactorily crystallized even when they are passed through the usual spinning and/or orientation steps. For this reason, additional problems arise when putting them into practical use. For instance, the tensile strength and dimensional stability of poly(lactic acid) are insufficient.

In addition, the higher the molecular weight of the foregoing poly(oxy-acids), the slower the rate of the decomposition thereof. Thus, it is necessary to produce poly(lactic acid) and poly(glycolic acid) whose molecular weight is controlled to control the decomposition speed of these polymers. However, the production of such polymers requires a lot of labor and the use of highly advanced techniques which require a great deal of skill. For this reason, the use of poly(oxy-acids) has been limited to medical applications, such as absorbent sutures and cosmetic applications. Accordingly, there has been a strong desire for a production process, which is inexpensive or economical, and does not require any skilled technique.

As discussed above, a suture of silk differs from sutures of poly(oxy-acids), such as poly(lactic acid) and poly(glycolic acid), which are decomposed into water and carbon dioxide in vivo. Accordingly, there is a strong desire for the development of a biodegradable material whose biodegradability in vivo can be controlled, which does not suffer from any problem concerning the biological safety, whose production cost is very low, which can biologically be decomposed without producing any cytotoxic products, which does not form any harmful substance such as formaldehyde as a by-product, and which is safe to the biological tissues.

The silk protein, which can be used as a raw material for the foregoing silk suture, is a naturally occurring polymer material produced through the biosynthesis of silkworms, which is excellent in the biological compatibility with the biological tissues and has good molding properties. Therefore, if by-products of silk, obtained in the process for preparing raw silk and silk products, are used as starting material for the sutures, one can save the cost of raw materials. Moreover, silk proteins include a large number of active sites rich in chemical reactivity. Therefore, the fields of application (such as the use as medical materials) can be widely extended if a technique, which permits the control of the biodegradability or biochemical properties of silk fibroin, can be developed, for instance, through hybrid processings and/or chemical modification. For this reason, there has been a strong desire for the development of a novel biodegradable material, which can be used effectively in the medical field, and which uses biopolymers from insects as starting materials and secondary substances capable of being combined (hybrid or hybridized with the former composite materials).

SUMMARY OF THE INVENTION

Accordingly, it is generally an object of the present invention to solve the problems associated with the foregoing conventional techniques. More specifically, it is an object of the present invention to provide a biodegradable biopolymer material consisting of a silk protein excellent as a polymeric substrate; a hybridized biodegradable biopolymer material comprising the silk protein and a specific secondary substance hybridized together and having unique characteristic properties not observed for the silk protein alone; a method for the preparation of the same; and functional materials consisting of the foregoing biodegradable biopolymer materials, such as a metal ion-adsorbing material, a sustained release carrier for a useful substance, a biological cell-growth substrate, and a biodegradable and water absorbable material.

The silk fibers from domesticated silkworm and wild silkworm are fibrous materials produced and spun by silkworms. They have strong resistance to chemicals, for instance, chemical agents and enzymes, since they have fibrous structures, as determined by the X-ray diffraction analysis. This is why the silk fiber from domesticated silkworm is classified as biologically non-absorbent material. The inventors of this invention have conducted various studies to provide a material comprising such a silk protein having good biodegradability, while making use of the excellent biochemical properties of the silk protein. The inventors also developed a technique for preparing a novel material whose biodegradability can be controlled by using silk fibroin from domesticated silkworm as a starting material and combining the starting material with a specific secondary substance. The inventors have further inspected for degradation behavior observed for a novel composite material obtained during the development process when acting an enzyme on the composite material. The inventors have found that a biopolymer material possessing biodegradability can be provided and have thus completed the present invention.

The biodegradable biopolymer material of the present invention is characterized in that it consists of silk fibroin from domesticated silkworm; silk fibroin from wild silkworm; a composite material comprising silk fibroin from domesticated silkworm and silk fibroin from wild silkworm; or a composite material comprising either silk fibroin from domesticated silkworm or silk fibroin from wild silkworm and at least one secondary substance selected from the group consisting of cellulose, chitin, chitosan, chitosan derivatives, keratin from wool and polyvinyl alcohol.

In this respect, the biodegradable biopolymer material may be capable of being biologically degraded by the action of at least one enzyme selected from the group consisting of proteases, collagenases and chymotrypsin.

The shape of the biodegradable biopolymer material may be fibrous, membrane-like, powdery, gel-like or porous.

The method for the preparation of a biodegradable biopolymer material according to the present invention comprises the steps of applying, onto the surface of a substrate, an aqueous solution of silk fibroin from domesticated silkworm, an aqueous solution of silk fibroin from wild silkworm, an aqueous mixed solution containing an aqueous solution of silk fibroin from domesticated silkworm and an aqueous solution of silk fibroin from wild silkworm or an aqueous mixed solution comprising either an aqueous solution of silk fibroin from domesticated silkworm or an aqueous solution of silk fibroin from wild silkworm and an aqueous solution of at least one secondary substance selected from the group consisting of cellulose, chitin, chitosan, chitosan derivatives, keratin from wool and polyvinyl alcohol; and then drying the applied solution to dryness to form a film-like biodegradable biopolymer material, wherein if using the aqueous mixed solution, the aqueous solutions as the constituents of the aqueous mixed solution are uniformly admixed together by stirring them such that they do not undergo any gelation, precipitation and/or coagulation reaction to thus prepare the aqueous mixed solution.

Moreover, a powdery biodegradable biopolymer material of the present invention can be prepared by freezing the foregoing aqueous solution of silk fibroin from domesticated silkworm, the foregoing aqueous solution of silk fibroin from wild silkworm or the foregoing aqueous mixed solution, and then drying the frozen aqueous solution under a reduced pressure. The mixed aqueous solution is prepared by the mixing method used above. Further, a gel-like biodegradable biopolymer material of the present invention can be prepared by adjusting the pH value of the foregoing aqueous solution of silk fibroin from domesticated silkworm, the foregoing aqueous solution of silk fibroin from wild silkworm or the foregoing aqueous mixed solution to a level falling within the acidic region, and then coagulating the entire aqueous solution to give a gel-like biodegradable biopolymer material. Incidentally, a porous substance can be prepared by subjecting the gel-like product of the biodegradable biopolymer material to lyophilization.

In the preparation of the foregoing aqueous mixed solution, the concentrations of the aqueous solution of silk fibroin from domesticated silkworm, the aqueous solution of silk fibroin from wild silkworm, and the aqueous solution of the secondary substance preferably range from 0.1 to 5% w/v, respectively. If the concentration is less than 0.1% w/v, the amount of the aqueous solutions required for the preparation of the composite material increases. This is not preferred for operation efficiency. If the concentration exceeds 5% w/v, it is difficult to uniformly admix two solutions and, as a result, it is impossible to prepare any composite material having uniform quality.

The metal ion-adsorbing material according to the present invention consists of a biodegradable biopolymer material, which is silk fibroin from domesticated silkworm; silk fibroin from wild silkworm; a composite material comprising silk fibroin from domesticated silkworm; silk fibroin from wild silkworm; or a composite material comprising either silk fibroin from domesticated silkworm or silk fibroin from wild silkworm and at least one secondary substance selected from the group consisting of cellulose, chitin, chitosan, chitosan derivatives, keratin from wool and polyvinyl alcohol. The metal ions may be anti-bacterial metal ions, such as silver, copper and cobalt ions or metal ions present in waste water.

The sustained release carrier for a useful substance according to the present invention consists of a biodegradable biopolymer material, which is silk fibroin from domesticated silkworm; silk fibroin from wild silkworm; a composite material comprising silk fibroin from domesticated silkworm and silk fibroin from wild silkworm; or a composite material comprising either silk fibroin from domesticated silkworm or silk fibroin from wild silkworm and at least one secondary substance selected from the group consisting of cellulose, chitin, chitosan, chitosan derivatives, keratin from wool and polyvinyl alcohol. It is also characterized in that it can gradually release the useful substance supported on the biodegradable biopolymer material while being biodegraded by the action of a protease, chymotrypsin or a collagenase. The biodegradable biopolymer material is preferably a porous substance.

The living cell-growth substrate according to the present invention consists of a biodegradable biopolymer material, which is silk fibroin from domesticated silkworm; silk fibroin from wild silkworm; a composite material comprising silk fibroin from domesticated silkworm and silk fibroin from wild silkworm; or a composite material comprising either silk fibroin from domesticated silkworm or silk fibroin from wild silkworm and at least one secondary substance selected from the group consisting of cellulose, chitin, chitosan, chitosan derivatives, keratin from wool and polyvinyl alcohol. The substrate is used for effectively and economically growing living cells.

The biodegradable water absorbable material according to the present invention consists of a biodegradable biopolymer material, which is silk fibroin from domesticated silkworm; silk fibroin from wild silkworm; a composite material comprising silk fibroin from domesticated silkworm and silk fibroin from wild silkworm; or a composite material comprising either silk fibroin from domesticated silkworm or silk fibroin from wild silkworm and at least one secondary substance selected from the group consisting of cellulose, chitin, chitosan, chitosan derivatives, keratin from wool and polyvinyl alcohol.

The term "biodegradation" as used herein means any reaction including, for instance, a digestion or hydrolysis reaction of silk fibroin, and/or the secondary substance into small molecules through the action of an enzyme and a digestion reaction into amino acids. Accordingly, an enzyme may degrade the substrate into small molecules through reactions other than digestion in the present invention, but the enzyme may conveniently be referred to as a protease (proteolytic enzyme).

DESCRIPTION OF THE PREFERRED EMBODIMENTS

In the present invention, raw materials for use in the preparation of an aqueous solution containing silk fibroin from silk protein fibers may, for instance, be silk fibers from domesticated or wild silkworms. The silk fibroin of the silk fiber obtained from domesticated silkworm usable herein may be silk fibroin as a silk protein. For instance, the silk protein may be from larvae of domesticated silkworm (*Bombyx mori*) reared in farmhouses and larvae of KUWAGO (*Bombyx mandarina* or mulberry wild silkworm), as a relative species of the domesticated silkworm. Examples of silk fibroin from wild silkworm usable herein are silk fibroin obtained from larvae of *Antheraea pernyi, Antheraea yamamai, Antheraea militta, Antheraea assama, Philosamia cynthia ricini* and *Philosamia cynthia pryeri*. Alternatively, raw materials for preparing the silk fibroin aqueous solution may be by-products from domesticated and wild silkworms, silk fibers, silk fiber products and aggregates of silk fibers, in addition to the foregoing silk fibers.

As described above, the secondary substance to be hybridized with the silk fibroin from domesticated or wild silkworm is at least one member selected from the group consisting of cellulose, chitin, chitosan, chitosan derivatives, keratin from wool and polyvinyl alcohol.

An aqueous solution of silk fibroin from domesticated silkworm is admixed with an aqueous solution of silk fibroin from wild silkworm. Alternatively, an aqueous solution of silk fibroin from domesticated silkworm or an aqueous solution of silk fibroin from wild silkworm is admixed with an aqueous solution of the secondary substance. This is followed by extending the resulting mixed aqueous solution over the surface of a substrate of, for instance, polyethylene, and then solidifying the extended solution by drying it to produce a biodegradable biopolymer material. The biodegradable biopolymer material produced is a composite material (or a hybrid material) of the silk fibroin from domesticated silkworm and the silk fibroin from wild silkworm, or a composite material of the silk fibroin from domesticated silkworm or the silk fibroin from wild silkworm with the secondary substance. Biodegradable biopolymer materials may be prepared from an aqueous solution containing only silk fibroin from domesticated silkworm and an aqueous solution containing only silk fibroin from wild silkworm by repeating the procedures used above.

The preparation of an aqueous solution of silk fibroin from domesticated silkworm, an aqueous solution of silk fibroin from wild silkworm, a membrane of silk fibroin from domesticated silkworm, and a membrane of silk fibroin from wild silkworm will be described in detail. A method for the preparation of a hybrid (composite material) using an aqueous mixed solution comprising an aqueous solution of silk fibroin from domesticated silkworm or an aqueous solution of silk fibroin from wild silkworm and an aqueous solution of each secondary substance or cellulose, chitin, chitosan, chitosan derivatives, keratin from wool or polyvinyl alcohol will also be detailed below.

(A) Preparation of Aqueous Solution of Silk Fibroin from Domesticated Silkworm and Membrane of Silk Fibroin from Domesticated Silkworm An aqueous solution of pure silk fibroin from domesticated silkworm may be prepared by the following method:

First, cocoon fibers produced and spun by domesticated silkworm are boiled in an alkaline aqueous solution of a neutral salt, such as sodium carbonate to remove sericin, to prepare silk fibroin fibers as the entity of the domesticated silkworm silk fibers. Then, the resulting silk fibroin fiber is dissolved in a concentrated aqueous solution of a neutral salt and heated to form a silk fibroin aqueous solution. This silk fibroin aqueous solution contains the silk fibroin and a large quantity of ions from the neutral salt. The aqueous solution is poured into a cellulose membrane for dialysis. Then, both ends of the membrane are tied up with sawing threads and dialyzed against tap water or pure water for a desired period of time ranging from 2 to 5 days to give an aqueous solution of pure domesticated silkworm silk fibroin. Aqueous solutions of silk fibroin having a variety of concentrations can be prepared by partially evaporating the water of the resulting silk fibroin aqueous solution or by diluting the resulting silk fibroin aqueous solution with water.

The aqueous solution of domesticated silkworm silk fibroin thus prepared can be extended over a substrate, such as a polyethylene membrane, followed by solidification of the extended layer of the silk fibroin solution through evaporation to dryness at room temperature to give a domesticated silkworm silk fibroin membrane.

In addition, the domesticated silkworm silk fibroin aqueous solution can be prepared by adding domesticated silkworm silk protein fibers (silk fibers) to a concentrated aqueous solution of a neutral salt, such as calcium chloride, calcium nitrate, lithium bromide or lithium thiocyanate, and then heating the mixture to dissolve the silk fibers in the aqueous solution. The concentration of the neutral salt in the aqueous solution ranges from about 5 to 9M, and it is sufficient to heat the mixture to a temperature ranging from about 25 to 70° C., preferably 25 to 60° C., for the dissolution of the silk fibers. If the dissolution temperature exceeds 70° C., the molecular weight of the silk protein is reduced, the resulting material loses its polymeric characteristics, and, as a result, the molding properties of the material may be considerably impaired. The dissolution time is preferably 1 to 20 minutes. Among the foregoing neutral salts, lithium salts satisfactorily dissolve the domesticated silkworm silk protein fibers and are excellent in solubilizing the domesticated silkworm silk fibroin fibers. Lithium bromide is preferred. For instance, an aqueous lithium bromide solution having a concentration of not less than 8M, and preferably not less than 8.5M, would permit dissolution of domesticated silkworm silk protein fibers by the treatment at a temperature of not less than 55° C. for a time of not less than 15 minutes.

(B) Preparation of Aqueous Solution of Silk Fibroin from Wild Silkworm and Membrane of Silk Fibroin from Wild Silkworm To prepare an aqueous solution of wild silkworm silk fibroin from silk fibers from wild silkworms, such as those from *Antheraea pernyi* and *Antheraea yamamai*, the wild silkworm cocoon fibers are immersed in an aqueous solution of sodium peroxide in a predetermined amount with respect to the mass thereof, and boiled for a desired time period to form wild silkworm silk fibroin fibers. The resulting silk fibroin fibers are dissolved in an aqueous solution of a neutral salt having a high solubilization ability. Then, the resulting aqueous solution is dialyzed in the same manner as the domesticated silkworm silk fiber above to give an aqueous solution of pure wild silkworm silk fibroin. This preparation method is described in more detail below.

In the preparation of an aqueous solution of wild silkworm silk fibroin by dissolving wild silkworm silk fibers, the silk sericin covering the surface of the wild silkworm cocoon fibers should be removed by a method different from the method used for refining the domesticated silkworm silk sericin. This is because tannin is also adhered to the surface of the wild silkworm silk fibers and the sericin is insolibilized due to the cross-linking action of the tannin. It is, for instance, necessary to immerse the wild silkworm cocoon fibers in about 50 volumes of a 0.1% sodium peroxide aqueous solution on the basis of the mass of the cocoon fibers and to then subject the cocoon fibers to a boiling treatment, for instance, at 98° C. for one hour, in order to remove the sericin and tannin. The wild silkworm silk fibroin fibers from which the sericin and tannin have been removed are then dissolved in an aqueous solution of a neutral salt having a high solubilization ability, such as lithium thiocyanate. The solution of the wild silkworm silk fibroin fibers in the aqueous neutral salt solution is poured into a cellulose membrane for dialysis. Then, both ends of the membrane are tied up with sawing threads and dialyzed against tap water or pure water maintained at room temperature for a desired period of time ranging from 2 to 5 days to completely remove the lithium ions and to give an aqueous solution of pure wild silkworm silk fibroin.

The aqueous solution of pure wild silkworm silk fibroin can be extended over a substrate, such as a polyethylene membrane, followed by solidification of the extended layer of the silk fibroin solution through evaporation to dryness at room temperature to give a wild silkworm silk fibroin membrane.

If the silk proteins from domesticated silkworm and those from wild silkworm can be sufficiently admixed together in the form of aqueous solutions, a composite material of these silk proteins may be prepared by solidifying an aqueous mixed solution of these components through evaporation to dryness. The resulting hybrid membrane may possess characteristic properties, such as biodegradability, transparency, adhesion stability and other biochemical properties, different from those observed for the materials from domesticated silkworm silk fibroin alone and wild silkworm silk fibroin alone. We will explain the method for preparing a hybrid membrane of the domesticated silkworm silk fibroin and the wild silkworm silk fibroin starting from the aqueous solutions of domesticated silkworm silk fibroin and wild silkworm silk fibroin.

(C) Hybrid Membrane of Domesticated Silkworm Silk Fibroin and Wild Silkworm Silk Fibroin Desired amounts of the aqueous solution of domesticated silkworm silk fibroin and the aqueous solution of wild silkworm silk fibroin prepared above are digested into a beaker and carefully and gently mixed by stirring using a glass rod in such a manner that the aqueous solution never undergoes gelation. The mixed aqueous solution prepared can be extended over a substrate such as a polyethylene membrane, followed by solidification of the extended layer of the silk fibroin solution through evaporation to dryness at room temperature to give a transparent hybrid membrane. The concentrations of the aqueous solution of domesticated silkworm silk fibroin and the aqueous solution of wild silkworm silk fibroin are preferably on the order of 0.1 to 3% w/v and particularly preferably 0.4 to 2% w/v, respectively.

The blending of an aqueous solution of domesticated silkworm silk fibroin or an aqueous solution of wild silkworm silk fibroin with an aqueous solution of a secondary substance as detailed below may be carried out in the same manner used above.

In this respect, a method for the preparation of a hybrid of domesticated silkworm silk fibroin and silk fibroin from *Antheraea pernyi* has already been reported by the inventors of this invention (M. Tsukada et al., Journal of Applied Polymer Science, 1994, 32: 1175-1181). However, this article does not include any description, which teaches and/or suggests the biodegradability of the hybrid.

(D) Hybrid Membrane of Domesticated or Wild Silkworm Silk Fibroin and Cellulose

A hybrid membrane consisting of domesticated silkworm silk fibroin and cellulose can be prepared by admixing the foregoing aqueous solution of the domesticated silkworm silk fibroin and an aqueous solution of cellulose according to the following method.

First, domesticated silkworm silk fibroin fibers and commercially available powdery cellulose (available from Fluka Company) free of any particular purification treatment are separately dissolved in cuprammonium ($[Cu(NH_3)_4](OH)_2$) aqueous solution to form respective aqueous solutions. Then, these two aqueous solutions are admixed in a desired mixing ratio (domesticated silkworm silk fibroin fibers/cellulose) by careful and gentle stirring in such a manner that the mixture never undergoes any gelation, precipitation and/or solidification. The mixed aqueous solution thus prepared is gently extended over a substrate such as a glass plate placed on a horizontal plane. A mixed solution containing acetone and acetic acid is then carefully added to the surface of the extended mixed aqueous solution to remove the metal complex present in the mixed aqueous solution while solidifying the domesticated silkworm silk fibroin and cellulose. Thereafter, the solidified mixture is washed with a mixed solution of glycerin and water and then with water, followed by drying the mixture at room temperature to give a hybrid membrane containing domesticated silkworm silk fibroin and cellulose.

A hybrid membrane containing wild silkworm silk fibroin can be prepared by the same procedures used above in the preparation of the hybrid membrane containing the domesticated silkworm silk fibroin.

In this respect, the inventors of this invention and the collaborators have already reported a method for the preparation of a hybrid of domesticated silkworm silk fibroin and cellulose. (see G. Freddi et al., Journal of Applied Polymer Science, 1995, 56: 1537-1545). However, this article does not include any description, which teaches and/or suggests the biodegradability of the hybrid.

(E) Hybrid Membranes of Domesticated or Wild Silkworm Silk Fibroin and Chitin, Chitosan and Chitosan Derivatives A hybrid membrane comprising domesticated silkworm silk fibroin and chitin, chitosan or a chitosan derivative can be prepared by admixing an aqueous domesticated silkworm silk fibroin solution and an aqueous solution of chitin, chitosan or a chitosan derivative according to the following method. The chitosan derivative usable in the present invention is not restricted to any specific one and may be, for instance, chitin, carboxylated carboxy methyl chitin (also referred to as "CMK") from chitosan, Na salt of carboxy methyl chitin and glycol chitosan.

The chitin used in the present invention may be, for instance, from a marine crustacean, such as a prawn or a black tiger, or chitin covering the crust of an insect. The crust of a crustacean or an insect comprises inorganic substances, such as calcium carbonate and proteins. Therefore, chitin may be isolated by the removal of contaminants other than chitin according to any currently known method. Moreover, it is also convenient to use a commercially available powdery product of chitin (Wako Pure Chemical Industries, Ltd.).

Chitin may be converted into water-soluble one according to the following method. First, powdery chitin is suspended in a concentrated aqueous caustic alkali (such as sodium hydroxide) solution and stirred over a desired period of time under reduced pressure. Then, the resulting powdery chitin is charged into a concentrated aqueous caustic alkali solution containing a surfactant such as sodium dodecyl sulfate, stirred and allowed to stand overnight at a low temperature (for instance, −20° C.). Alternatively, the resulting powdery chitin is suspended in liquid ammonia (−33° C.) and then metal potassium is added to the resulting suspension to prepare alkali chitin in which the hydrogen atoms on the C6 and C3 hydroxyl groups of chitin are substituted with sodium or potassium. The alkali chitin prepared is compressed and dispersed in ice crushed into fine pieces, followed by the sulfidation of the chitin through the addition of carbon disulfide to obtain a chitin sulfide. An aqueous solution can be prepared using this sulfide.

Moreover, the alkali chitin may be reacted with an epoxy compound, an allyl or an alkali halide to give an o-allyl derivative or an o-alkyl derivative. Further, the alkali chitin may be reacted with ethylene chlorohydrin (2-chloroethanol) to give ethylene glycol chitin or with chloroacetic acid to give o-(carboxymethyl) chitin. If ethylene glycol chitin is reacted with a concentrated caustic alkali aqueous solution (for instance, a 40% sodium hydroxide aqueous solution) under desired reaction conditions (for instance, 100/C for 5 hours) with stirring, the acetamide groups present on the chitin molecules are hydrolyzed into free amino groups to give water-soluble glycol chitosan. Chitosan derivatives including the glycol chitosan can be easily dissolved in an aqueous acid solution having a wide concentration range, such as an aqueous acetic acid solution.

A mixed aqueous solution obtained by the addition of a domesticated silkworm silk fibroin aqueous solution to the foregoing aqueous glycol chitosan solution may be extended over, for instance, a polyethylene substrate, and then solidified through evaporation to dryness to prepare a transparent and soft composite material (a hybrid membrane) comprising domesticated silkworm silk fibroin and glycol chitosan. Hybrid membranes may likewise be prepared by the use of aqueous solutions of other chitosan derivatives or an aqueous solution of water-solubilized chitin, instead of the foregoing glycol chitosan aqueous solution, according to the same procedures used above.

In the case of wild silkworm silk fibroin, hybrid membranes may be prepared by repeating the procedures used above in connection with the domesticated silkworm silk fibroin.

(F) Hybrid Membrane of Domesticated or Wild Silkworm Silk Fibroin and Wool Keratin Hybrid membrane of domesticated or wild silkworm silk fibroin and wool keratin usable in the present invention may be, for instance, wool keratin fibers as well as aqueous keratin solutions and aqueous S-carboxy methyl keratin (CMK) solutions, which can be prepared as follows. These aqueous solutions may be prepared according to the conventionally known methods.

To solubilize wool yarns, the Cystine cross linkings are cleaved using a reducing agent (such as mercapto-ethanol or thioglycollic acid) in a nitrogen gas atmosphere or keratin molecules are reduced and solubilized. If mercapto-ethanol is used, it is preferred to carry out the reduction in a urea solution. In this case, the concentration of urea ranges from 7.5 to 8.8 M, preferably 7.8 to 8 M. If thioglycollic acid is used, it is desirable to add NaCl to the reaction system in an amount of 1 to 4%.

When using mercapto-ethanol, which may act as a reducing agent, wool yarns are immersed in a urea solution having a concentration specified above, followed by degassing. Mercapto-ethanol is added to the mixture in an amount of 3 to 5 mL per 10 g of wool yarns at a temperature of not more than 45° C., desirably 20 to 25° C., in a nitrogen gas atmosphere. The resulting mixture is stirred over a predetermined period of time (for instance, about 3 hours). Thus, keratin molecules in wool yarns are reduced and keratin molecules having SH groups are prepared. Then, the reaction system containing the keratin molecules having SH groups is digested into a cellulose membrane for dialysis. Next, both ends of the cellulose membrane are tied up with sawing threads and sufficiently dialyzed against pure water to remove the urea and the excess mercapto-ethanol to give an aqueous solution of the wool keratin. This aqueous wool keratin solution may be used as an aqueous solution of a secondary substance used in the present invention according to the same procedures used above.

Moreover, if the wool keratin carrying —SH groups obtained above is further reacted with an alkylation agent, for instance, any known alkylation agent such as an (substituted) alkyl halide to form an S-(substituted) alkyl keratin, the aqueous solution thereof may likewise be used in the present invention. This alkylation may be carried out according to any known method. The alkylation will be described below using iodoacetic acid as an alkylation agent by way of example. To the foregoing reduced keratin, iodoacetic acid is added (molecular weight: 185.95) in an amount ranging from 10 to 17 g per 10 g of the wool yarns in order to react them at a temperature ranging from 20 to 25° C. in a nitrogen gas atmosphere with stirring. After 1 to 2 hours, the pH value of the reaction system is adjusted to about 8.5, followed by dialysis against pure water to remove the excess iodoacetic acid to give an aqueous solution of S-carboxymethyl keratin.

To the aqueous solution of the reduced keratin or the aqueous solution of the S-carboxymethyl keratin, there can be added an aqueous solution of domesticated silkworm silk fibroin to give a mixed aqueous solution. The mixed aqueous solution is extended over the surface of a substrate such as a polyethylene substrate, and then the extended aqueous layer is dried to give a hybrid membrane of the reduced keratin, or the S-carboxymethyl keratin and the domesticated silkworm silk fibroin.

In the case of the wild silkworm silk fibroin, a hybrid membrane can be prepared according to the same procedures used for preparing the hybrid membrane of the domesticated silkworm silk fibroin.

(G) Hybrid Membrane of Domesticated Silkworm Silk Fibroin or Wild Silkworm Silk Fibroin and Polyvinyl Alcohol Polyvinyl alcohol (PVA having an average degree of polymerization of about 2000 available from Wako Pure Chemical Co., Ltd.) is charged into hot water, followed by careful dissolution using a stirring machine to form an aqueous PVA solution having a desired concentration (for instance, a 0.5% w/v PVA aqueous solution). An appropriate amount of an aqueous solution of domesticated silkworm silk fibroin is added to this PVA aqueous solution. The resulting mixture is allowed to stand at room temperature for not less than 30 minutes to form a complex aqueous solution of domesticated silkworm silk fibroin and PVA. The complex aqueous solution can be extended over the surface of a substrate, such as a polyethylene substrate, and the moisture of the extended aqueous layer is evaporated over a whole day and night to give a transparent hybrid membrane of PVA and the domesticated silkworm silk fibroin.

In the case of the wild silkworm silk fibroin, a hybrid membrane can be prepared according to the same procedures used for preparing the hybrid membrane of the domesticated silkworm silk fibroin.

The inventor of this invention and the collaborators have already reported a method for the preparation of a hybrid membrane of PVA and domesticated silkworm silk fibroin (see, M. Tsukada et al., Journal of Applied Polymer Science, 1994, 32: 243-248). However, this article does not include any disclosure that refers to or suggests the biodegradability of the hybrid membrane.

As discussed above, the silk proteins from domesticated silkworm, wild silkworm and secondary substances may be admixed together in their aqueous solution states and hybrid membranes can be prepared from the resulting aqueous mixed solutions. The resulting hybrid membranes may show biochemical characteristic properties such as biodegradability, transparency (light transmission properties) and a cell-growth ability, which are different from those observed for a material simply comprising domesticated silkworm silk fibroin or wild silkworm silk fibroin. In addition, the hybrid membrane also possesses, for instance, excellent metal ion-adsorbing properties and resistance to peeling. To obtain a hybrid membrane from an aqueous solution of domesticated silkworm silk fibroin, an aqueous solution of wild silkworm silk fibroin, and aqueous solutions of secondary substances in this case, it is sufficient that the concentration of each aqueous solution falls within the range of from 0.1 to 5% w/v, as specified above, preferably 0.4 to 3% w/v, to obtain hybrid membranes having uniform quality. In this respect, the aqueous solution of domesticated silkworm silk fibroin and the aqueous solution of wild silkworm silk fibroin; and the aqueous solution of domesticated silkworm silk fibroin or the aqueous solution of wild silkworm silk fibroin and the aqueous solution of secondary substances may be admixed together in any rate. Therefore, the mixing ratio of these components in the resulting composite may, if desired, be set at an arbitrarily level.

To admix domesticated silkworm silk fibroin and wild silkworm silk fibroin, or an aqueous solution of domesticated silkworm silk fibroin or an aqueous solution of wild silkworm silk fibroin with an aqueous solution of a secondary substance, it is sufficient to gently admix these aqueous solutions by stirring with a glass rod. If these solutions are admixed rapidly, vigorously or violently, a shear stress is applied to the silk fibroin molecules, the aqueous solutions undergo coagulation and it is sometimes observed that these solutions are not uniformly admixed.

The biodegradable biopolymer material of the present invention may have any shape, such as a sheet-like, membrane-like, powdery, bead-like, gel-like, fibrous, tubular or hollow thread-like shape.

In the present invention, the biodegradability of a biodegradable biopolymer material can be evaluated by treating it with a buffering solution containing a peptidase in a predetermined concentration for a predetermined period of time. More specifically, the biodegradable biopolymer material is digested (or hydrolyzed) through the treatment thereof with an enzyme-containing aqueous dissociation solution prepared by dissolving an enzyme having a desired activity in a desired buffering solution at 37° C. for a predetermined period of time. The degree of biodegradation is evaluated by calculating the extent of the biodegradable biopolymer material digested by the enzyme on the basis of the weight change of the sample.

The degree of digestion is greatly influenced by the kinds of enzymes used, the concentrations of the enzyme, the time required for the enzyme-decomposition and/or the kinds of materials to be treated. Moreover, the degree of digestion also greatly varies depending on whether the material is silk protein fibers or silk protein membranes. The silk protein fiber produced by silkworm has a fibrous structure peculiar thereto and a large density of hydrogen bonds formed between fibrous molecules. Therefore, it is hardly hydrolyzed, even when introducing it into an aqueous solution of a peptidase. For this reason, the silk protein fiber can be used as a sample for a biodegradation test without any pre-treatment. In contrast, a silk fibroin membrane, or the like as a silk protein membrane prepared after once dissolving the silk protein fibers in a neutral salt solution, will swell through the absorption of moisture and will ultimately dissolve. In the biodegradation test, the dissociation behavior of the material in a buffering solution containing an enzyme is examined. Therefore, the silk fibroin membrane prepared cannot be directly subjected to such a biodegradation test. It is necessary to subject the membrane to an insolubilization treatment in order to use it as a test sample. The material or membrane may be insolibilized by, for instance, immersion in an aqueous solution of an alcohol, such as methanol or ethanol; or by the use of a conventionally known epoxy compound or an aldehyde, such as formalin. For instance, the membrane may be insolibilized by immersing it in a 20 to 80% methanol aqueous solution for a time usually ranging from 5 to 10 minutes, preferably a 40 to 60% methanol aqueous solution for 5 to 10 minutes. More specifically, it is sufficient to lightly immerse the membrane in a 50% (v/v) methanol aqueous solution at room temperature for not less than one minute and then dry it in air at room temperature.

Moreover, almost all of the composite materials, other than the foregoing silk fibroin membrane, are insoluble in water immediately after preparation by the process for evaporation to dryness. Usually, these materials are desirably insoluble in water in many applications. It is sufficient, in such cases, to make them insoluble in water by the treatment with methanol. The composite material of domesticated silkworm silk fibroin and cellulose or that of domesticated silkworm silk fibroin and polyvinyl alcohol is water-soluble immediately after the preparation thereof. If the composite material is treated with methanol, the silk fibroin becomes insoluble in water. However, the cellulose and polyvinyl alcohol components are not converted into water-insoluble components through such a methanol treatment. Accordingly, it is preferred to subject such composite materials to a cross-linking reaction with a reagent having a strong cross-linking ability such as formalin.

Any peptidase (digestive enzyme) may be used in the present invention. The peptidase may be one which cleaves a distinct site of a substrate or one whose cleaving site on a substrate cannot be specified. The biodegradable biopolymer material of the present invention may be biodegraded by the action of an enzyme such as proteases, collagenases, and chymotrypsin. As described above, it is desirable for the evaluation of the biodegradability using these enzymes to use a buffering solution having a desired pH value capable of maintaining the maximum enzyme activity. No specific combination of an enzyme and a buffering solution used in the enzymatic decomposition is required. Examples of preferred combinations of enzymes and buffering solutions are a collagenase and 50 mM TES (buffering solution) or 50 mM $CaCl_2$ (pH 7.4); chymotrypsin and 50 mM Tris (buffering solution) or 5 mM $CaCl_2$ (pH 7.8); and a protease and 40 mM potassium phosphate (buffering solution) (pH 7.5). A borate buffering solution having a low ionic strength is preferably used as such a buffering solution and the pH thereof roughly ranges from 7 to 8.

The concentration of the protein hydrolase (or peptidase) aqueous solution may vary depending on the kinds of proteins used as substrates and in general ranges from 0.1 to 0.8 mg/mL, preferably 0.2 to 0.5 mg/mL. If the enzyme concentration is less than 0.1 mg/mL, the efficiency of the digestion is insufficient. If it exceeds 0.8 mg/mL, the biodegradation experiment becomes less advantageous from an economical standpoint.

One of the inventors of this invention has previously prepared domesticated silkworm silk fibroin membrane and domesticated silkworm silk fibers by dissolving and biodegrading domesticated silkworm silk fibroin fibers, to clarify the biodegradation behavior thereof over time (see N. Minoura et al., Biomaterials, 1990, 11 (August): 430-434). In this article, it is confirmed that domesticated silkworm silk fibroin membrane is hydrolyzed to a significant extent in a protease solution, while the domesticated silkworm silk fibers are not hydrolyzed to any significant degree. However, silk material from wild silkworm contains a silk protein having a primary structure completely different from the chemical structure of the domesticated silkworm silk fibers. There has not yet been reported any information concerning the biodegradability of wild silkworm silk fibers and wild silkworm silk fibroin membrane.

According to the present invention, a powdery biodegradable biopolymer material can be prepared by lyophilizing an aqueous solution of domesticated silkworm silk fibroin, an aqueous solution of wild silkworm silk fibroin, an aqueous mixed solution containing an aqueous solution of domesticated silkworm silk fibroin and an aqueous solution of wild silkworm silk fibroin or an aqueous mixed solution comprising either an aqueous solution of domesticated silkworm silk fibroin or an aqueous solution of wild silkworm silk fibroin and an aqueous solution of a secondary substance, such as cellulose, according to any known method. More specifically, these aqueous solutions are frozen at a temperature of about $-10°$ C. Then, the frozen solutions are allowed to stand in an atmosphere maintained at a reduced pressure to remove the moisture present in the sample and to thus form a powdery material. In addition, a gel-like biodegradable biopolymer material may be obtained by adjusting the pH value of the aqueous solution of each sample to fall within the acidic region, for instance, not more than 4.4, to coagulate the entire aqueous solution and convert it into a gel. A membrane-like biodegradable biopolymer material may be obtained by extending the aqueous solution of each sample over a substrate, such as a polyethylene substrate or a glass plate, followed by evaporating the extended layer to dryness for a sufficient period of time.

All of the foregoing powdery, gel-like and membrane-like biodegradable biopolymer materials are soluble in water. Therefore, they can, if desired, be insolibilized in water by immersing in an aqueous alcohol solution as discussed above.

The biodegradability of the biodegradable biopolymer material of the invention through the action of a hydrolase is determined by the concentration of the enzyme, the buffering solution used, the digestion time, the degree of water-insolubilization and the content of the domesticated silkworm silk fibroin. For this reason, the biodegradability of a material can be improved by reducing the water-insolubility or increasing the water-solubility, and increasing the content of the domesticated silkworm silk fibroin in the material. A silk material free of any fibrous structure, such as silk fibroin membrane, is quite susceptible to digestion with an enzyme, in contrast to the silk fibroin fibers. In particular, the biodegradability of a composite material (hybrid) is determined by the degree of water insolubility of the domesticated and wild silkworm silk fibroins, the secondary substance selected, the mixing ratio of the domesticated or wild silkworm silk fibroin to the secondary substance, the enzyme selected, the enzyme concentration and the treating time. Therefore, the conditions for preparing hybrids, the mixing ratios or the biodegradation conditions can be appropriately changed or selected depending on the desired purposes.

A biodegradable biopolymer material having a good biocompatibility can be prepared by hybridizing or blending silk fibroin with an organic polymer (secondary substance). An organic polymer is excellent in the affinity to biological tissues, but is hardly decomposed with a protein hydrolase.

The biodegradable biopolymer material of the present invention may be a hybrid of materials, both of which serve as substrates for enzymes, such as proteases, collagenases and chymotrypsin; or a hybrid of a polymer material capable of serving as a substrate and a secondary substance, which cannot serve as a substrate. Examples of proteins capable of serving as substrates for these three kinds of enzymes are domesticated silkworm silk fibroin, wild silkworm silk fibroin and wool keratin. When hybridizing these materials capable of serving as substrates for the enzymes with naturally occurring polymers, which cannot serve as substrates of these enzymes, such as cellulose, chitin, chitosan, chitosan derivatives and polyvinyl alcohol, there is observed a tendency that the amount of the hybrid biodegraded is gradually reduced as the content of the naturally occurring polymer in the hybrid increases.

For instance, in the case of a hybrid membrane consisting of domesticated silkworm silk fibroin and cellulose, the domesticated silkworm silk fibroin is easily decomposed by the action of a protease. Therefore, the higher the content of the domesticated silkworm silk fibroin, the easier the control of the degree of biodegradation of the hybrid. However, the behavior of the domesticated silkworm silk fibroin for a cellulase is completely contrary to the behavior discussed above. Accordingly, the higher the content of the cellulose, the smaller the amount of the hybrid biodegraded as a whole. Thus, a biodegradable biopolymer material having a desired rate of biodegradation can be prepared by changing the mixing ratio of the protein capable of serving as a substrate for an enzyme used to a secondary substance, which can never serve as a substrate for the enzyme.

The biopolymer usable herein is not restricted to any specific one and may be, for instance: silk proteins from domesticated and wild silkworms (such as silk fibroins and silk sericin) or keratins from animals (such as wool keratin); collagen; and gelatin. The present invention may use, for instance, silk proteins from domesticated and mulberry wild silkworms, or silk proteins from *Antheraea yamamai, Antheraea pernyi, Philosamia cynthia ricini* and *Philosamia cynthia pryeri* Silkworms as wild silkworms. Such biopolymers may be silk fibers, silk fiber products from domesticated and wild silkworms or fibrous aggregates thereof, or keratin fibers from animals and keratin fiber products.

The biodegradable biopolymer material of the present invention is useful as a metal ion-adsorbing material. In particular, when immersing a composite material (hybrid) as a biodegradable biopolymer material of the present invention in an aqueous solution containing antibacterial metal ions, such as silver, copper and/or cobalt ions, the composite material adsorbs a large quantity of these metal ions. Therefore, the composite material carrying metal ions can be useful as an antibacterial material. Alternatively, when immersing the biodegradable biopolymer material in waste water, the material adsorbs various kinds of metal ions present in the waste water (for instance, base metal ions, such as $Cu^{2+}$, $Ni^{2+}$, $Vo^{2+}$, $Zn^{2+}$, $Co^{2+}$ and $Al^{3+}$, and ions of rare earth metals, such as Yb, Nd, Pr and La). Accordingly, the material is also useful as a material for adsorbing metal ions present in waste water. The metal ions adsorbed on the material may be recovered or disposed, according to circumstances.

A useful substance, such as a water-soluble medicine or a pharmaceutically active substance, can be included in or immobilized on the biodegradable biopolymer material, in particular, the composite material of the present invention. The resulting product may be implanted or embedded in, for instance, a living body, so that the product implanted may gradually release the medicine or pharmaceutical component, while the material is decomposed and/or deteriorated through digestion with, for instance, a protease present in the body fluid. Therefore, the material of the present invention can be used as a sustained release carrier for useful substances. In this respect, the silk fibroin fiber from domesticated or wild silkworm may be used to make the biodegradability thereof light, or to make a membrane-like sample, which is obtained by dissolving domesticated or wild silkworm silk fibers using a neutral salt, desalting the resulting solution using a cellulose dialysis membrane and then evaporating the dialyzed solution to dryness to obtain an easily decomposable material. The membrane of domesticated silkworm silk fibroin is more easily biodegraded than the membrane of wild silkworm silk fibroin. Therefore, it is sufficient to increase the content of the wild silkworm silk fibroin to form a hardly biodegradable composite material comprising domesticated and wild silkworm silk fibroins.

As described above, when using the biodegradable biopolymer material, in particular, the composite material of the present invention while embedding it in the living body, the material is ultimately decomposed into small molecules, such as water and carbon dioxide, by the action of enzymes present in the body, such as proteases, chymotrypsin and collagenases, and finally excreted outside the body. A hybrid membrane with easily biodegradable domesticated silkworm silk fibroin may be biodegraded within a relatively short period of time even when embedding the same in the living body unlike hardly biodegradable domesticated silkworm silk fibroin fibers. Therefore, the hybrid may be used for the temporal assist of the healing of remediable damaged biological tissues or as a sustained release carrier for drugs as discussed above. Such in vivo degradable and absorbable material may be used in a variety of applications, such as the suture of incised and/or wound portions, arrest of hemorrhage, bone fixation, a clue for tissue-regeneration and a means for preventing adhesion.

The hybridization of domesticated or wild silkworm silk fibroin with a secondary substance would provide such a conspicuous effect that the resulting hybrid shows, on it surface, excellent biochemical properties, which have never been observed for the surface of the domesticated or wild silkworm silk fibroin or the secondary substance. For instance, the rate of cell-growth on the surface of the hybrid is higher than that observed on the surface of a product consisting simply of domesticated or wild silkworm silk fibroin or a secondary substance. Moreover, the hybridization of domesticated silkworm silk fibroin with wild silkworm silk fibroin or the hybridization of a secondary substance, such as cellulose, with domesticated or wild silkworm silk fibroin would provide a hybrid or composite material having improved moldability and transparency, as compared with those observed for a membrane simply consisting of domesticated or wild silkworm silk fibroin, and would possess excellent cell adhesion properties. In addition, the composite material has a high wear resistance and the rate of cell-growth on the composite surface is improved, as compared with that observed on the surface of a membrane consisting of a single protein. Accordingly, such a composite material may be used as cell-growth materials in the field of biochemistry.

Moreover, cellulose derivatives may be used in food additives, cosmetics, additives for drugs and pharmaceutical preparations, such as anti-thrombotic agents. Therefore, the composite materials consisting of domesticated silkworm silk fibroin and cellulose may be used in applications similar to those for the cellulose.

The biodegradable biopolymer material of the present invention possesses water-absorbing properties, which make the material applicable as a water-absorbable resin used in, for instance, disposable hygienic goods and household goods, water cut-off agents, soil conditioners, dewing inhibitors, and water-retention agents for agriculture and horticulture. The present invention would also permit the supply of a water-absorbing material having such biodegradability for a low price without requiring any complicated steps. For this reason, the material of the present invention can be applied to any fields of applications identical to those for the conventionally known water-absorbing resins. For instance, the material of the present invention can be used in a wide variety of fields, such as hygiene (typically use as a diaper and a sanitary good), medical service (for instance, use in cataplasms), civil engineering and architecture (for instance, use as an agent for gelling sludge), foods, industries, and agriculture and horticulture (for instance, use as a soil conditioner and a water-retention agent).

The present invention will be described below in more detail with reference to the following Examples and Comparative Examples, but the present invention is not limited to these specific Examples. In the following descriptions, the term "%" means w/v unless otherwise specified.

Various test methods used in the following description will be described in detail.

(1) Evaluation of Mechanical Properties

The strength and elongation at the break of each silk fiber upon the breakage thereof were determined using INSTRON (Autograph AGS-5D available from Shimadzu Corporation) under the following measurement conditions: the length of a sample to be tested of 50 mm, the rate of extension of 10 mm/min and the chart full scale of 250 g. In this respect, each measured value means the average of 20 measurements repeatedly carried out.

(2) Methods for the Adsorption of Metal Ions on Biodegradable Biopolymer Material and for Quantitative Determination thereof Each sample to be examined was immersed in a 0.5 mM aqueous metal salt solution containing potassium nitrate (the pH value thereof was adjusted to 11.4 by the addition of aqueous ammonia) at room temperature for 30 hours to adsorb metal ions on the sample. In this respect, metal ions were adsorbed on the sample by immersing the latter in an aqueous metal salt solution (the pH value thereof was controlled to 8.5).

The metal ions adsorbed on each test sample were analyzed using a plasma atomic absorption spectrometer (ICP-AES) available from Perkin-Elmer Company. More specifically, each test sample (5 to 10 mg) was completely hydrolyzed with 2 mL of a 65% aqueous nitric acid solution in a microwave hydrolysis furnace (MDS-81DCCEM), 10 mL of water was added to the hydrolyzed sample prior to the analysis and then the resulting mixture was subjected to the analysis in the ICP-AES. The amount of metal ions adsorbed on each sample is expressed in terms of the amount of metal ions (in mM unit) per unit mass of the sample.

(3) Decomposition Treatment with Enzyme

An enzyme used in the biodegradation experiment was dissolved in a buffering solution optimum for the digestion. This solution was charged into a 100 mL volume sterilized glass beaker, followed by the addition of each test sample and decomposition thereof with the enzyme at 37° C. for a predetermined time. The degree of biodegradation of each test sample observed after the treatment over a predetermined time is expressed in terms of the rate of the residual sample (by weight) (hereunder referred to as "rate of remaining weight") irrespective of the presence of the enzyme. More specifically, the rate of remaining mass is given by the following equation: [(Wi−We)/Wi]H 100(%) wherein Wi and We represent the masses of each sample determined before and after the biodegradation test, respectively.

Thus, the term "rate of remaining mass" herein used means the rate (%) of the residual sample (by weight), even after the digestion to the sample weight prior to the biodegradation. The smaller the value, the greater the amount of the sample hydrolyzed or the higher the biodegradability of the sample.

(4) Biodegradation Rate

The digestion rate observed when hydrolyzing each test sample with an enzyme was evaluated by the following method. The digestion rate is herein defined to be the amount (%) of the sample biodegraded during the biodegradation procedure carried out over 50 hours relative to the initial mass of each test sample or the mass of the test sample at the initiation of the biodegradation test, which is defined to be 100. Therefore, the higher the digestion rate observed for a specific sample, the higher the biodegradability of the sample.

(5) Fourier Transform Infrared Absorption Spectra

The absorption spectra of each test sample concerning the molecular shape thereof were analyzed using an FT-IR (Fourier Transform Infrared Absorption Spectra) measuring device available from Perkin-Elmer Company. This analysis was carried out over a wave number range of from 2000 to 400 $cm^{-1}$ and the number of scanning was 20.

(6) Test for Wear Resistance

A GAKUSHIN Type color fastness to rubbing tester Model II was used as a rub tester. A polyethylene terephthalate (PET) substrate coated with a thin membrane of each sample, selected from a variety of silk proteins, was fitted to the rub tester. The wear resistance test was carried out by reciprocating a friction element having an applied load of 500 g over 10 times in such a manner that the sample fitted to the friction element is lightly rubbed with that fixed to a test table under the action of a predetermined load. The sample was subjected to the FT-IR spectroscopic measurement before and after the wear resistance test to determine the wave numbers of absorption peaks. A sample thin membrane on the PET substrate whose FT-IR absorption peak shows reduction of its intensity after the friction operation is judged to be easily peelable.

(7) Crystallinity Index of Domesticated Silkworm Silk Fibroin Membrane

The crystallinity index of a domesticated silkworm silk fibroin membrane hydrolyzed with a variety of enzymes was evaluated according to the following method: In this method, the Fourier transform infrared absorption spectra (FT-IR) measuring device used was a Nicolet-150P measuring device available from Nicolet Instruments, Madison, Wis. equipped with an ATR diamond cell (SPECAC). In the IR spectroscopy, the peak strengths of amide band III at wave numbers of 1230 $cm^{-1}$ and 1260 $cm^{-1}$ were determined and the crystallinity index (CI) was determined according to the following formula. In this respect, the value of CI is a numerical value corresponding to the ratio of the peak strengths and does not have any unit.

$$CI = I[1230\ cm^{-1}]/I[1260\ cm^{-1}]$$

(8) Amino Acid Analysis

Various protein materials corresponding to various biodegradation times were subjected to the following amino acid analysis. Each test sample used herein was prepared by hydrolyzing each protein material with a 6N hydrochloric acid solution at 105° C. for 24 hours. The amino acid analysis was carried out using RP-HPLC.

(9) Test for Antibacterial Activity Against Vegetative Pathogenic Bacteria:

As vegetative pathogenic bacteria, the bacterial canker of tomato (scientific name: *Corynebacterium michiganense* pv. *michiganense*) was selected. This bacterial canker is typical of the universal vegetative pathogenic bacteria, whose resistant bacteria may be easily induced and may attack various kinds of plants, or which is a polyxeny putrefactive bacterium and is one of the rare gram positive bacteria in the vegetative pathogenic bacteria. The antibacterial activity of each test sample (composite membrane) was evaluated on the basis of the growth-inhibitory effect thereof on the vegetative pathogenic bacterium.

The evaluation of antibacterial effects in the following Examples was carried out according to the following method.

Method for Examining Antibacterial Activity against Bacterium 25 mL of semi-synthesized Wakimoto Medium or King Medium B, which had been dissolved with heating and then maintained at 55° C., was admixed with 2 mL of the bacterium to be assayed (concentration: 109/mL). The mixture was poured into a petri dish to solidify the same in a plate-like shape. A sample membrane of about 1 cm square was placed on this plate-like medium containing the bacterium and the whole sample was closely adhered to the culture medium. The resulting assembly was maintained at a temperature ranging from 20 to 25° C. The size of the inhibitory circle appearing at the periphery of the sample was practically determined in the unit of mm in predetermined intervals to evaluate the bacterial growth-inhibitory effect observed on the culture medium in the proximity to the sample to be assayed and to thus confirm the presence of any antibacterial activity or evaluate the relative superiority on the basis of the change in the size of the inhibitory circle observed.

(10) Test for Insect's Cell Growth

Ae cells from *Antheraea pernyi* or Bm cells from domesticated silkworm were cultivated using a culture medium comprising Grace Medium (G8142 available from Sigma Company) containing 5% powdered body fluid of silkworm and 5% fetal calf serum (available from Gibco Company), to which 1% penicillin-streptomycin mixed antibiotic had been supplemented. After 2 days, the number of insect cells present in the cell culture medium was determined using a hemocytometer to analyze the conditions of the Ae and Bm cells proliferated on the surfaces of various kinds of composite materials whose silk fibroin contents were different from one another.

(11) Determination of Molecular Weight

Each fibrous or membrane-shaped sample used in the biodegradation test was dissolved in a small amount of a 50% (w/v) aqueous solution of lithium thiocyanate at 40° C. over 30 minutes. Then, the resulting solution was diluted with 50 mM sodium phosphate buffering solution, a 0.15 M aqueous solution of potassium chloride (pH 7.2) and a 5M aqueous solution of urea. The diluted solution was digested into a dialysis membrane of cellulose (Spectra/Por 6, MW 10=3.5 kDa, available from Spectrum Company). Then, the solution in the membrane was dialyzed against the same buffering solution over 48 hours. After the dialysis, the dialyzate was diluted with distilled water to a silk fibroin concentration of 1 mg/mL, filtered through a 0.2:m porous filter immediately thereafter, and then analyzed by the size exclusion chromatography technique. Waters chromatographic system used herein is equipped with a pump (mod. 510) provided with a temperature control device, an injector (mod. U6K) and a refractive index detector (mod. 410). This system is provided with software for chromatography (Maxima 820 (Waters)) and GPC Lanter software. The column temperature was set at 30/C. The column used herein was Shodex Protein KW-804 (Waters, 8 H 300 mm) packed with porous silica gel coated with hydrophilic OH groups (pre-column, Shodex Protein KW-G, 6 H 50 mm). The amount of the sample loaded on the column ranged from 50 to 100:1 and the exit velocity was set at 0.5 mK/min. The analysis was carried out using distilled water as the moving phase and optimally using a 50 mM sodium phosphate buffering solution, a 0.15 M aqueous solution of potassium chloride (pH 7.2) and a 5M solution of urea.

The reference markers for molecular weight used herein were kits for HMW and LMW gel filtration correction (available from Pharmacia Biotech.). In this connection, the detection was carried out at 254 nm using a UV detector.

Technical terms concerning the molecular weight determination will hereunder be described:

Molecular Weight: This is a weight average molecular weight or a value (molecular weight) determined by integrating the area surrounded by the elution curve. This is dependent on the whole peptides present in the sample and requires a variety of molecular weights.

Peak Molecular Weight: This is the molecular weight corresponding to the peak of the elution curve. This corresponds to the molecular weight of peptides present in the sample and requires the maximum population. In this case, the molecular weight distribution is not taken into consideration.

EXAMPLE 1

Preparation of Aqueous Solution of *Bombyx mori* Silk Fibroin and *Bombyx mori* Silk Fibroin Membrane First, cocoon fibers from *Bombyx mori* silkworm were immersed into a mixed aqueous solution containing 0.2% Marcel Soap and 0.05% sodium carbonate. The mixture was boiled at 98° C. for 30 minutes to remove the sericin adhering the outer layer of the cocoon fibers and to prepare silk fibroin fibers. The resulting silk fibroin fibers (10 g) were immersed in an 8.5M lithium bromide aqueous solution at a temperature of not less than 55° C. for 15 minutes to dissolve the silk fibroin fibers. This aqueous neutral salt solution was poured in a dialysis membrane of cellulose and both ends of the membrane were tied up with sawing threads. The solution was then dialyzed against tap water maintained at 5° C. for 2 days to completely remove the lithium ions and bromide ions present therein and to thus give an aqueous solution of pure *Bombyx mori* silk fibroin. Aqueous solutions of silk fibroin having a variety of concentrations were prepared by partially evaporating the water of the resulting silk fibroin aqueous solution or diluting it with water. These aqueous solutions were used in the following Examples.

The silk fibroin aqueous solution thus prepared was cast dried on a polyethylene substrate at room temperature to form a *Bombyx mori* silk fibroin membrane.

EXAMPLE 2

Preparation of Aqueous Solution of Silk Fibroin from *Antheraea pernyi* and Membrane of *Antheraea pernyi* Silk Fibroin First, cocoon fibers from *Antheraea pernyi* were immersed in a 0.1% aqueous solution of sodium peroxide at 98° C. for one hour to remove the silk sericin and tannin covering the surface of the cocoon fibers from *Antheraea pernyi* and to prepare *Antheraea pernyi* silk fibroin fibers (material-to-liquor ratio 1:50). The *Antheraea pernyi* silk fibroin fibers whose sericin and tannin had been removed in advance were dissolved in an aqueous lithium thiocyanate solution. The resulting aqueous solution was poured into a dialysis membrane of cellulose and both ends of the membrane were tied up with sawing threads. The solution was dialyzed against tap water maintained at room temperature for 2 days to completely remove the lithium ions and thiocyanate ions present therein and to give an aqueous solution of pure *Antheraea pernyi* silk fibroin.

The *Antheraea pernyi* silk fibroin aqueous solution prepared was cast dried on a polyethylene substrate at room temperature to form an *Antheraea pernyi* silk fibroin membrane.

EXAMPLE 3

Hybrid Membrane of *Bombyx mori* Silk Fibroin and *Antheraea pernyi* Silk Fibroin Predetermined amounts of the aqueous solutions of *Bombyx mori* silk fibroin and *Antheraea pernyi* silk fibroin prepared in Examples 1 and 2, respectively, were added to a beaker. These solutions were carefully admixed together by gentle stirring with a glass rod in such a manner that the aqueous solutions never underwent any gelation (or precipitation). The mixed aqueous solution thus prepared was cast dried on a polyethylene substrate at room temperature to form a transparent hybrid membrane.

The concentrations of both aqueous solutions of *Bombyx mori* silk fibroin and *Antheraea pernyi* silk fibroin were set at a level of 0.1 to 3 wt %. The use of aqueous solutions having a concentration falling within the range would permit the appropriate control of the amounts of these aqueous solution required for the preparation of such a hybrid membrane and efficient operations. In addition, the use thereof permitted the uniform mixing of these two liquids, and as a result, a hybrid membrane having uniform quality could be obtained.

EXAMPLE 4

Hybrid Membrane of *Bombyx mori* Silk Fibroin and Cellulose

First, *Bombyx mori* silk fibroin fibers and commercially available powdery cellulose free of any particular purification (available from Fluka Company) were separately dissolved in a cuprammonium solution ($[Cu(NH_3)_4](OH)_2$) to prepare corresponding aqueous solutions. Then, these two kinds of aqueous solutions were admixed together with gentle stirring such that the *Bombyx mori* silk fibroin fibers/cellulose composition was equal to 80/20, 60/40, 40/60 or 20/80. The mixed aqueous solution thus prepared was gently cast dried on a glass plate arranged on a horizontal plane. A mixed solution containing acetone and acetic acid (4:1 (v/v)) was carefully added to the surface of the mixed aqueous solution to remove the metal complex present in the mixed aqueous solution while solidifying or coagulating the *Bombyx mori* silk fibroin and the cellulose. Thereafter, the resulting membrane was washed with a mixed solution containing glycerin and water (7:13 (v/v)), then with water, and then dried at room temperature to give a hybrid membrane of *Bombyx mori* silk fibroin and cellulose. The resulting membrane had a thickness ranging from about 10 to 30:m.

EXAMPLE 5

Hybrid Membrane of *Bombyx mori* Silk Fibroin and Chitin, Chitosan Derivatives

In this Example, the aqueous solution of *Bombyx mori* silk fibroin prepared in Example 1 was admixed with an aqueous solution of chitin or a chitosan derivative as a secondary substance to prepare a hybrid membrane of *Bombyx mori* silk fibroin and chitin or a chitosan derivative as a secondary substance.

First, powdery chitin was suspended in a 42% aqueous solution of sodium hydroxide and stirred for 4 hours under reduced pressure. Then, the resulting powdery chitin was charged into a 60% aqueous sodium hydroxide solution containing sodium dodecyl-sulfate, stirred and then allowed to stand at −20° C. overnight. Alternatively, the resulting powdery chitin was suspended in liquid ammonia (−33° C.) and then metal potassium was added to the suspension to give alkali chitin. The alkali chitin thus prepared was compressed, dispersed in finely divided ice and then sulfurized by the addition of carbon disulfide to thus give chitin sulfide. The aqueous solution of this sulfide was used as an aqueous solution of a secondary substance.

Separately, the alkali chitin and ethylene chlorohydrin (2-chloroethanol) were reacted under the known reaction conditions to give ethylene glycol chitin. This chitin was treated in a 40% aqueous sodium hydroxide solution at 100° C. for 5 hours with stirring to form water-soluble glycol chitosan. The glycol chitosan was dissolved in an aqueous acetic acid solution and the resulting solution was used as an aqueous solution of a secondary substance.

Then, to each of the aqueous solution of sulfide and the aqueous solution of glycol chitosan prepared according to the foregoing methods, there was added an aqueous solution of *Bombyx mori* silk fibroin prepared according to the method used in Example 1 to give each corresponding aqueous mixed solution. This aqueous mixed solution was cast dried on a polyethylene substrate to form a transparent, soft membrane-like composite material comprising chitin sulfide or glycol chitosan and *Bombyx mori* silk fibroin.

EXAMPLE 6

Hybrid Membrane of *Bombyx mori* Silk Fibroin and Wool Keratin

To dissolve wool yarns, Cystine cross linkings thereof were cleaved using mercapto-ethanol or thioglycollic acid in a nitrogen gas atmosphere to solubilize the keratin molecules through reduction. When using mercapto-ethanol, the reduction was carried out in a urea solution having a concentration of 8M. When using thioglycollic acid, the reduction was carried out by the addition of 4% NaCl.

More specifically, degreased wool yarns were immersed in a urea solution having a concentration of 8M, followed by degassing, adding mercapto-ethanol in an amount of 5 mL per 10 g of wool yarns at a temperature of 25° C. in a nitrogen gas atmosphere and stirring over 3 hours to reduce the wool keratin molecules and to give wool keratin carrying SH groups. Then, the resulting wool keratin was dialyzed against pure water to remove the urea and the excess mercapto-ethanol and to give an aqueous solution of wool keratin. This aqueous wool keratin solution was used as an aqueous solution of a 40 secondary substance.

Moreover, to 10 g of the reduced wool keratin obtained according to the foregoing method, 15 g of iodoacetic acid at 25° C. was added with stirring in a nitrogen gas atmosphere to react the reduced wool keratin and the iodoacetic acid. After 2 hours, the pH value of the reaction system was adjusted to about 8.5. The resulting reaction solution was poured into a dialysis membrane of cellulose and both ends of the membrane were tied up with sawing threads. The reaction solution was dialyzed against pure water to remove the excess iodoacetic acid present therein and to give an aqueous solution of S-carboxymethyl keratin. This aqueous solution was used as an aqueous solution of a secondary substance.

To each of the aqueous reduced wool keratin solution and the aqueous solution of S-carboxymethyl keratin prepared according to the foregoing procedures, there was added an aqueous solution of *Bombyx mori* silk fibroin prepared according to the procedures used in Example 1 to give each corresponding aqueous mixed solution. This aqueous mixed solution was cast dried on a polyethylene substrate to form a hybrid membrane of reduced keratin or S-carboxymethyl keratin and *Bombyx mori* silk fibroin.

EXAMPLE 7

Hybrid Membrane of *Bombyx mori* Silk Fibroin and Polyvinyl Alcohol

Polyvinyl alcohol (PVA) was added to hot water of 85° C. and carefully dissolved therein using a stirring machine. The resulting solution was allowed to stand at room temperature for 30 minutes to give a 0.5% aqueous solution of PVA. To this PVA aqueous solution, there was added a 0.3% w/v aqueous solution of *Bombyx mori* silk fibroin prepared according to the procedures used in Example 1. The resulting aqueous mixed solution was cast dried on a polyethylene substrate over a whole day and night to form a transparent hybrid membrane of PVA and *Bombyx mori* silk fibroin.

EXAMPLE 8

Peel Resistance of Silk Fibroin Membrane with Respect to PET Substrate

A silk fibroin membrane was adhered to the surface of a polyethylene terephthalate (PET; trade name: Tetoron) membrane according to the following method. The foregoing Tetoron membrane was immersed in a 5% aqueous *Bombyx mori* silk fibroin (BF) solution prepared according to the procedures used in Example 1, a 3% aqueous *Antheraea pernyi* silk fibroin (TF) solution prepared according to the procedures used in Example 2 or an equivalent mixed aqueous solution of the 5% aqueous *Bombyx mori* silk fibroin (BF) solution and the 3% aqueous *Antheraea pernyi* silk fibroin (TF) solution, withdrawn therefrom and then dried at room temperature. Each of these membranes (hereunder abbreviated as "PET/BF", "PET/TF", "PET/(BF+TF)" respectively) was subjected to the determination of ATR (Attenuated Total Reflection) spectra. This ATR spectroscopic analysis was carried out using an ATR infrared spectrophotometer (FT-IR5300 available from Nippon Bunko K.K.) (Resolution 2; Number of Scanning: 32; gain: 100; using Apdization CS). In addition, a friction element was reciprocated 10 times on a membrane sample using an abrasion machine. Then, the membrane sample was again subjected to the ATR spectroscopic analysis. The results observed for the sample prior to the friction test are listed in the following Table 1.

TABLE 1

| Sample | Wave Number (cm$^{-1}$) and Absorption Intensity |
|---|---|
| PET | 1711 (vs), 1408 (s), 1338 (s) |
| PET/BF | 1687 (s), 1657 (vs), 1554 (s), 1408 (s), 1338 (s), 650 (s) |
| PET/TF | 1688 (s), 1655 (vs), 1408 (s), 1338 (s), 620 (s) |
| PET/(BF + TF) | 1789 (s), 1657 (vs), 1655 (vs), 1408 (s), 1338 (s), 650 (w), 620 (s) |

In Table 1, symbols "vs, s" and "w" indicate that the spectral intensities are very strong, strong and weak, respectively.

As will be clear from the data listed in Table 1, the ATR spectra observed for PET/BF include absorption peaks ascribable to PET (1408 and 1338 cm$^{-1}$) and absorption peaks ascribable to *Bombyx mori* silk fibroin (1657 and 650 cm$^{-1}$), which are superimposed to one another. Moreover, the ATR spectra observed for PET/TF include absorption peaks ascribable to *Antheraea pernyi* silk fibroin (1655 and 620 cm$^{-1}$) in addition to those ascribable to PET, which are overlapped to one another. The ATR spectra observed for PET/BF and PET/TF obtained after the friction element was reciprocated 10 times thereon were identical to those observed for PET prior to the adhesion of these silk fibroin membranes.

The foregoing results clearly indicate that when the PET/BF and PET/TF laminate surface are treated in an abrasion machine, the BF or TF membrane on the surface of PET substrate is scraped off during the reciprocating motions of the friction element. In the case of the PET/(BF+TF) laminate, however, the absorption peaks ascribable to BF and the absorption peaks ascribable to TF still remain in the ATR spectra observed for the PET/(BF+TF) laminate even after the laminate surface is treated in an abrasion machine. This clearly indicates that BF+TF is certainly adhered to the surface of the PET substrate and scarcely peeled off therefrom even when mechanically rubbed.

In addition, a PET substrate having a size of 2 cm H 3 cm was immersed in an aqueous solution containing simply *Bombyx mori* or *Antheraea pernyi* silk fibroin and a mixed aqueous solution prepared by admixing an aqueous solution of *Bombyx mori* silk fibroin and an aqueous solution of *Antheraea pernyi* silk fibroin by carefully and gently stirring with a glass rod at room temperature in a desired mixing ratio (at 25° C. for 10 minutes). Then, the PET covered with each solution was withdrawn from each aqueous solution and cast dried at room temperature. To make the silk protein membrane on the PET substrate insoluble, the coated PET substrate with silk fibroin was immersed in a 50% aqueous solution of methanol for 5 minutes, withdrawn therefrom and then dried at room temperature. The processed membrane thus prepared was subjected to the same ATR spectrometric analysis described above in connection with the foregoing membrane free of any insolubilization treatment.

As a result, absorption peaks were observed ascribable to *Bombyx mori* silk fibroin membrane in addition to those ascribable to the PET substrate in the case of the membrane simply consisting of *Bombyx mori* silk fibroin; absorption peaks ascribable to *Antheraea pernyi* silk fibroin membrane in addition to those ascribable to the PET substrate in the case of the membrane simply consisting of *Antheraea pernyi* silk fibroin; and absorption peaks ascribable to *Bombyx mori* and *Antheraea pernyi* silk fibroin membranes in addition to those ascribable to the PET substrate in the case of the hybrid membrane. This fact clearly indicates that the surface of the PET substrate is covered with a membrane consisting of *Bombyx mori* silk fibroin, *Antheraea pernyi* silk fibroin or a hybrid thereof.

Then, the peel resistance of various coated membrane with respect to a PET substrate were evaluated according to the foregoing method using PET substrates whose surfaces were covered with a membrane of *Bombyx mori* silk fibroin, a membrane of *Antheraea pernyi* silk fibroin and a hybrid membrane of *Bombyx mori* and *Antheraea pernyi* silk fibroins, respectively.

As a result, it was found that the membrane simply consisting of *Bombyx mori* or *Antheraea pernyi* silk fibroin had a tendency to be slightly easily peeled off from the PET substrate, while the hybrid membrane had a tendency that it was hardly peeled off therefrom and was excellent in the adhesion stability. In other words, it was found that the interaction between the surface of the PET substrate and the hybrid membrane (BF+TF membrane) is higher than those observed between the surface of the PET substrate and the BF membrane and between the surface of the PET substrate and the TF membrane. More specifically, a BF or TF membrane adhered to a PET substrate is easily peeled off from the PET substrate when any mechanical frictional force is applied to each laminate, but a hybrid membrane is strongly interacted with a PET substrate and therefore, the former is hardly peeled off from the latter.

EXAMPLE 9

Cell-growth Ability on Hybrid Membrane Surface

The cell-growth behaviors of *Bombyx mori* cells (Bm cells) and *Antheraea pernyi* cells (Ae cells) on the membrane surface were examined according to the method described above using a *Bombyx mori* silk fibroin membrane (BF membrane), an *Antheraea pernyi* silk fibroin membrane (TF membrane) and a hybrid membrane (BF+TF membrane) prepared according to the procedures used in Examples 1, 2 and 3, respectively. The results obtained indicate that both of these cells show almost the same tendency in the cell-growth behavior. Therefore, only the results observed for the Bm cells are summarized in the following Table 2.

TABLE 2

| Component of Membrane | Degree of Cell-Growth |
|---|---|
| BF | ± |
| TF | ± |
| BF + TF | + |

In Table 2, "±" means that the degree of cell-growth is almost identical to or slightly superior to that observed for the polystyrene surface as a control substrate and "+" means that the degree of cell-growth visually judged is superior to that observed for the polystyrene surface.

As will be seen from the results listed in Table 2, the degree of insect cell-growth observed on the surface of a culture medium covered with the hybrid membrane of BF and TF is higher than that observed on the surface of a culture medium covered with the *Bombyx mori* silk fibroin membrane (BF membrane) or the wild silkworm silk fibroin membrane (TF membrane).

EXAMPLE 10

Optimum Biodegradation Conditions

In this Example, it is intended to determine the optimum conditions for the biodegradation test carried out in the following Examples. This is because various conditions should be adjusted such that the enzyme used can maintain its maximum activity even when changing the kind and concentration of the enzyme. For instance, the kind of the buffering solution and the pH value should appropriately be selected.

The optimum conditions for evaluating the decomposition behavior of biodegradable biopolymer material with enzymes are as follows. The optimum conditions, such as the kinds of enzymes, enzyme activities and optimum pH values of buffering solutions, are summarized in the following Table 3. The biodegradation temperature was set at 37° C. As enzymes, three kinds of enzymes were used, chymotrypsin, collagenase and protease. The material-to-buffering solution ratio 1:250 was maintained and the biodegradation behavior was monitored or examined over 570 hours. The enzyme concentration was expressed in terms of the mass (mg) of each enzyme per 1 mL of the culture medium. The chymotrypsin, the collagenase (Type F) and the protease used were all available from Sigma Aldrich Japan Co., Ltd.

The buffering solutions used in this Example were TES (N-tris (hydroxymethyl)-methyl-2-aminoethane sulfonic acid available from Wako Pure Chemical Industries, Inc.) for the biodegradation tests using collagenase; tris(hydroxymethyl)-amino-methane(2-amino-2-hydroxymethyl-1,3-propanediol available from Wako Pure Chemical Industries, Inc.) for the biodegradation tests using chymotrypsin; and potassium phosphate buffering solution for the biodegradation tests using protease.

TABLE 3

| Enzyme | Enzyme Concn. (mg/mL) | Buffering Solution | Activity (units/mg solid) | pH |
|---|---|---|---|---|
| Collagenase | 0.2, 0.5 | 50 mL TES, 50 mM $CaCl_2$ | 1.8-2.2 | 7.4 |
| Chymotrypsin | 0.2, 0.5 | 50 mM Tris, 5 mM $CaCl_2$ | 40-60 | 7.8 |
| Protease | 0.2, 0.5 | 40 mM Potassium phosphate (pH7.5) | 5.7 | 7.5 |

EXAMPLE 11

In this Example, the biodegradation behaviors of *Bombyx mori* silk fibroin membrane or *Antheraea pernyi* silk fibroin membrane were investigated.

The cocoon layer of *Bombyx mori* was cut into pieces having a size of ¼ time the original one. The waxes and dyestuffs included in the sample were removed in a Soxhlet extractor using an ethanol/benzene mixed solution (1:2 v/v). Then, the cocoon fiber sample was charged into a mixed solution containing 0.2% Marcel Soap and 0.05% sodium carbonate. The mixture was then boiled at 98° C. for 30 minutes to remove sericin as an adhesive substance present in the outer layer of the cocoon fiber. At this stage, the material-to-liquor ratio was set at 1:100. Ten grams of *Bombyx mori* silk fibroin fibers thus prepared were immersed in a 8.5 M aqueous solution of lithium bromide at a temperature of not less than 55° C. for 15 minutes to solubilize the silk fibers. This aqueous neutral salt solution was poured into a dialysis membrane of cellulose and both ends of the membrane were tied up with sawing threads. The aqueous solution was then dialyzed against pure water maintained at room temperature for 4 days to completely remove the lithium and bromide ions present therein and to give an aqueous solution of *Bombyx mori* silk fibroin having a concentration of 0.2%.

Alternatively, cocoon fibers from *Antheraea pernyi* were degummed in a 0.1% aqueous sodium peroxide solution in an amount of 50 times the mass of the cocoon fibers at a temperature of 98° C. for one hour to remove sericin and tannin. The *Antheraea pernyi* silk fibroin fibers from which sericin and tannin had been removed were dissolved in an aqueous solution of lithium thiocyanate maintained at 55° C. The resulting aqueous solution was poured into a dialysis membrane of cellulose and both ends of the membrane were tied up with sawing threads. The aqueous solution was then dialyzed against pure water to give an aqueous solution of *Antheraea pernyi* silk fibroin having a concentration of 0.3%.

The 0.2% aqueous solution of *Bombyx mori* silk fibroin and the 0.3% aqueous solution of *Antheraea pernyi* silk fibroin prepared according to the procedures used above were separately cast dried on a polyethylene substrate at room temperature to form a *Bombyx mori* silk fibroin membrane (BF membrane) and an *Antheraea pernyi* silk fibroin membrane (TF membrane), respectively.

The *Bombyx mori* silk fibroin membrane and the *Antheraea pernyi* silk fibroin membrane thus prepared were proteolyticaly digested for the relation between the biodegradation behaviors by the action of a variety of enzymes and the biodegradation time (0, 24, 72, 240, 576 hours). The rates (%) of the residual sample weight as a function of the biodegradation time are summarized in the following Table 4. The enzyme concentration was set at 0.2 and 0.5 mg/mL.

digestion reaction thereof is advanced with the elapse of the biodegradation time. In this Example, the crystallinity index of each membrane was investigated in order to clarify any change in the fine structure of the *Bombyx mori* silk fibroin membrane during the biodegradation process.

The *Bombyx mori* silk fibroin membrane, which had been biodegraded with a variety of enzymes for a predetermined period of time, was evaluated for the crystallinity index (CI) according to the foregoing method. In this connection, CI has no dimension. The results thus obtained are listed in the following Table 5.

TABLE 4

| Sample | Enzyme (Concn.) | Biodegradation Time (hr.) | | | | |
|---|---|---|---|---|---|---|
| | | 0 | 24 | 72 | 240 | 576 |
| *Bombyx mori* Silk Fibroin Membrane | Control | 100 | 98 | — | — | — |
| | Collagenase (0.2 mg/mL) | 100 | 98 | 95.5 | 93.5 | 90 |
| | Collagenase (0.5 mg/mL) | 100 | 97.8 | 96.5 | 91.0 | 87.5 |
| | Chymotrypsin (0.5 mg/mL) | 100 | 90.9 | 90.5 | 89.7 | 90.6 |
| | Protease (0.2 mg/mL) | 100 | 81.8 | 75.6 | 71.6 | 54.5 |
| | Protease (0.5 mg/mL) | 100 | 72.7 | 43.5 | 44.4 | 27.9 |
| *Antheraea pernyi* Silk Fibroin Membrane | Protease (0.2 mg/mL) | 100 | 96.9 | 88.6 | 88 | 86.2 |
| | Protease (0.5 mg/mL) | 100 | 88.8 | 89.8 | 87.2 | 76.1 |

The enzyme concentrations listed in Table 4 are expressed in terms of the amount (mg) of each enzyme added to the biodegradation medium per 1 mL of the latter.

The data listed in Table 4 clearly indicate that the *Bombyx mori* silk fibroin membrane is susceptible to the digestion with protease and that in the biodegradation experiment at a protease concentration of 0.2 mg/mL, the rate of the residual sample weight is found to be 54.5% after the biodegradation time of 576 hours. On the other hand, when acting the same concentration of protease on the *Antheraea pernyi* silk fibroin membrane, the rate of the residual sample weight is found to be 86.2% after the biodegradation time of 576 hours. This indicates that the *Bombyx mori* silk fibroin membrane is more susceptible to the digestion with protease as compared with the *Antheraea pernyi* silk fibroin membrane.

EXAMPLE 12

Crystallinity Index

When the *Bombyx mori* silk fibroin membrane is biodegraded, the mass of the membrane undergoes changes and the

TABLE 5

| Enzyme (Concn.) | Biodegradation Time (hr.) | | | |
|---|---|---|---|---|
| | 0 | 72 | 240 | 408 |
| Collagenase (0.2 mg/mL) | 0.547 | 0.55 | 0.56 | 0.568 |
| Chymotrypsin (0.2 mg/mL) | 0.55 | 0.557 | 0.568 | 0.569 |
| Protease (0.2 mg/mL) | 0.547 | 0.585 | 0.594 | 0.601 |
| Protease (0.5 mg/mL) | 0.547 | 0.607 | 0.617 | 0.615 |

As will be clear from the data listed in Table 5, the amorphous region of the *Bombyx mori* silk fibroin membrane is digested through the digestion reaction with the enzyme and, as a result, the crystalline region thereof increases.

EXAMPLE 13

Biodegradation Behavior of Silk Fibers

The biodegradation behaviors of *Bombyx mori* silk fibers and *Antheraea pernyi* silk fibers were investigated on the basis of the rate of the residual sample weight according to the same procedures used in Example 11. The results obtained are summarized in the following Table 6.

TABLE 6

| Sample | Enzyme (Concn.) | Biodegradation Time (hr.) | | | | |
|---|---|---|---|---|---|---|
| | | 0 | 24 | 72 | 240 | 576 |
| *Bombyx mori* Silk Fiber | Control | 100 | 100 | — | — | — |
| | Collagenase (0.2 mg/mL) | 100 | 100 | 100 | 100 | 99 |
| | Collagenase (0.5 mg/mL) | 100 | 99.5 | 99 | 99 | 98 |
| *Bombyx mori* Silk Fiber | Control | 100 | 99 | — | — | — |
| | Chymotrypsin (0.2 mg/mL) | 100 | 99.5 | 99.5 | 99.3 | 99 |
| | Chymotrypsin (0.5 mg/mL) | 100 | 99 | 99 | 99 | 99 |
| *Bombyx mori* Silk | Control | 100 | 100 | — | — | — |

TABLE 6-continued

| Sample | Enzyme (Concn.) | Biodegradation Time (hr.) | | | | |
|---|---|---|---|---|---|---|
| | | 0 | 24 | 72 | 240 | 576 |
| Fiber | Protease (0.2 mg/mL) | 100 | 98.6 | 99.3 | 99.3 | 99.3 |
| | Protease (0.5 mg/mL) | 100 | 100 | 100 | 99.8 | 99.3 |
| *Antheraea pernyi* Silk Fiber | Control | 100 | 100 | — | — | — |
| | Collagenase (0.2 mg/mL) | 100 | 100 | 100 | 98 | 97 |
| | Collagenase (0.5 mg/mL) | 100 | 100 | 100 | 100 | 99 |
| *Antheraea pernyi* Silk Fiber | Control | 100 | 100 | — | — | — |
| | Chymotrypsin (0.2 mg/mL) | 100 | 100 | 99 | 99 | 98 |
| | Chymotrypsin (0.5 mg/mL) | 100 | 100 | 100 | 100 | 100 |
| *Antheraea pernyi* Silk Fiber | Control | 100 | 100 | — | — | — |
| | Protease (0.2 mg/mL) | 100 | 100 | 100 | 99.9 | 99.5 |
| | Protease (0.5 mg/mL) | 100 | 99.2 | 99.0 | 98.4 | 99.2 |

The results listed in Table 6 indicate that the *Bombyx mori* silk fiber and the 15 *Antheraea pernyi* silk fiber are scarcely biodegraded on the basis of the decreasing rate of the residual sample weight. However, the silk fiber may undergo changes in fine structures and may suffer deterioration in addition to weight changes during the biodegradation process. For this reason, the *Bombyx mori* silk fiber was evaluated for the deterioration during the biodegradation process on the basis of the strength and elongation according to the following method.

*Bombyx mori* silk fibers were added to a culture medium containing protease, collagenase or chymotrypsin. As such, they were biodegraded over a predetermined time period and then the changes with time of the strength and elongation at break of the silk fibers after the biodegradation were determined. The results thus obtained are summarized in the following Table 7.

TABLE 7

| | Biodegradation Time (hr.) | | | | |
|---|---|---|---|---|---|
| | 0 | 24 | 72 | 240 | 408 |
| Strength (N) | | | | | |
| Collagenase (0.2 mg/mL) | 4.68 | 3.60 | 4.12 | 3.86 | 3.64 |
| Chymotrypsin (0.2 mg/mL) | 4.68 | 3.83 | 3.72 | 3.97 | 3.78 |
| Protease (0.2 mg/mL) | 4.68 | 3.74 | 3.52 | — | 3.14 |
| Protease (0.5 mg/mL) | 4.68 | 3.83 | 3.77 | — | 3.23 |
| Elongation (%) | | | | | |
| Collagenase (0.2 mg/mL) | 32.7 | 26.3 | 25.1 | 25.7 | 23.5 |
| Chymotrypsin (0.2 mg/mL) | 32.7 | 28.1 | 27.8 | 26.4 | 25.8 |
| Protease (0.2 mg/mL) | 32.7 | 21.6 | 20.5 | — | 18.1 |
| Protease (0.5 mg/mL) | 32.7 | 24.1 | 23.2 | — | 19.0 |

In Table 7, the enzyme concentration is given in parentheses behind each corresponding enzyme name and it is expressed in terms of the amount of the enzyme (mg) per 1 mL of the culture medium. Moreover, the strength of the silk fiber expressed in N can be converted into that in kg on the basis of the equation: (numerical value of each strength)/9.81. In this Table, for instance, 4.68 N corresponds to 477.1 g.

The data listed in Table 7 clearly indicates that both the strength and the elongation of the silk fiber decrease with an increase of biodegradation time. The data listed in Table 6 indicates that the silk fiber is not biodegraded at first view, but it is clear that the deterioration of the silk fiber is in fact advanced due to the biodegradation.

EXAMPLE 14

Biodegradability of Hybrid Membrane

A hybrid membrane sample prepared from *Bombyx mori* silk fibroin (BF) and *Antheraea pernyi* silk fibroin (TF) according to the procedures used in Example 3 and a hybrid membrane prepared from *Bombyx mori* silk fibroin (BF) and cellulose (Cell) according to the procedures used in Example 4 were examined for the relation between the biodegradation time and the rate (%) of the residual sample weight observed when they are hydrolyzed with protease. The results thus obtained are listed in the following Table 8.

TABLE 8

| Sample | Presence of Enzyme | Biodegradation Time (hr.) | | | | |
|---|---|---|---|---|---|---|
| | | 24 | 72 | 240 | 408 | 572 |
| BF:TF (8:2) | present | 85.4 | 81.8 | 77.3 | 75.0 | 75.0 |
| BF:TF (8:2) | absent | 100 | 100 | 100 | 100 | 100 |
| BF:TF (6:4) | present | 85 | 84.2 | 84.2 | 84.2 | 78.9 |
| BF:TF (6:4) | absent | 95.4 | 95.4 | 94.4 | 100 | 100 |
| BF:TF (4:6) | present | 100 | 91.3 | 86.9 | 86.4 | 86.4 |
| BF:TF (4:6) | absent | 100 | 100 | 100 | 100 | 95.5 |
| BF:TF (2:8) | present | 100 | 100 | 96.9 | 97.1 | 96.9 |
| BF:TF (2:8) | absent | 100 | 100 | 100 | 100 | 95.5 |
| BF:Cell (8:2) | present | 86.4 | 87.9 | 51.7 | 50 | 52.1 |
| BF:Cell (8:2) | absent | 88.8 | 89.5 | 89.5 | 90 | 90 |
| BF:Cell (6:4) | present | 77.3 | 72 | 65.4 | 60.8 | 61.5 |
| BF:Cell (6:4) | absent | 94.1 | 96.7 | 97.1 | 100 | 96.9 |
| BF:Cell (4:6) | present | 78.6 | 75 | 73.0 | 73.3 | 73.3 |
| BF:Cell (4:6) | absent | 100 | 100 | 100 | 100 | 100 |
| BF:Cell (2:8) | present | 94.1 | 94.1 | 94.1 | 87.5 | 82.4 |
| BF:Cell (2:8) | absent | 94.4 | 100 | 100 | 100 | 100 |
| BF:Cell (0:10) | present | 97.5 | 94.1 | 100 | 97.1 | 97.7 |
| BF:Cell (0:10) | absent | 93.7 | 95.7 | 96.7 | 97.7 | 96.3 |

In the column entitled "Presence of Enzyme" in Table 8, each section specified by "absent" means the biodegradation experiment, which is conducted in an aqueous solution containing only a buffering solution and free of any proteolytic enzyme, while, each section specified by "present" means the biodegradation experiment, which is carried out in an enzyme-containing decomposition solution containing both protease and a buffering solution. In addition, "BF:TF (4:6)" means a hybrid membrane prepared by admixing an aqueous solution of *Bombyx mori* silk fibroin and an aqueous solution of *Antheraea pernyi* silk fibroin, such that the resulting mixed solution contains 40% *Bombyx mori* silk fibroin and 60% *Antheraea pernyi* silk fibroin, and then cast drying. "BF: Cell (8:2)" means a hybrid membrane prepared in such a manner that the resulting hybrid membrane comprises 80% *Bombyx mori* silk fibroin and 20% cellulose.

As will be seen from the data listed in Table 8, in the case of the hybrid membrane of *Bombyx mori* silk fibroin and *Antheraea pernyi* silk fibroin (BF: TF membrane) the hybrid membrane is hardly biodegradable as a whole, as the content of the *Antheraea pernyi* silk fibroin increases. Moreover, in the case of the hybrid membrane of *Bombyx mori* silk fibroin and cellulose (BF: Cell membrane), the hybrid membrane is likewise hardly biodegradable.

EXAMPLE 15

Hybrid Membrane of *Bombyx mori* Silk Fibroin and Wool Keratin

An aqueous solution of wool keratin was prepared as follows.

Pigments and greases contained in wool (64' S) from sheep belonging to the Merino species were removed by treating the same with a benzene/ethanol (50/50 (% by volume)) mixed solvent for 2.5 hours using a Soxhlet extractor.

A three-necked flask was used. The first neck thereof was connected to one end of a rubber tube, the other end of which was connected to a nitrogen gas cylinder for drying through a three-way cock. The second neck thereof was always occupied by a pH electrode assembly for the control of the pH value of the reaction system. The third or remaining neck or port was used for the introduction of any necessary reagent into the system. Wool yarns (8.18 g) from sheep of Merino species, which had been cut into short yarns having a yarn length of about 1 cm, were charged into the three-necked flask. Then, 450 mL of an 8M aqueous urea solution was added to the flask. The flask was purged with nitrogen gas, the pressure in the flask was reduced to about 45 mmHg for 15 minutes using an aspirator and then the pressure in the flask was abruptly returned to the atmospheric pressure, these operations being repeated three to four times. Thus, the air contained in the wool yarns present in the three-necked flask was completely removed so that the reaction of the aqueous urea solution with keratin molecules would be efficiently advanced. After the completion of the displacement with nitrogen gas, 4.8 mL of mercapto-ethanol as a reducing agent was added to the three-necked flask and the wool yarns were allowed to stand in the 8M aqueous urea solution over 2 to 3 hours. Then, about 100 mL of a 5N-KOH aqueous solution was added to the flask in small portions to thus adjust the pH value of the mixed aqueous solution in the flask to 10.5. The content of the flask was allowed to stand at room temperature for 3 hours until the wool yarns were completely dissolved in the aqueous solution to give an aqueous keratin solution. The resulting aqueous keratin solution was poured into a dialysis membrane of cellulose and both ends of the membrane were tied up with sawing threads. The aqueous keratin solution was then dialyzed against pure water for 2 days. The resulting aqueous keratin solution was subjected to drying through ventilation or, if desired, diluted with pure water to give an aqueous keratin solution having a desired keratin concentration.

The keratin in the 0.01% aqueous keratin solution thus prepared was subjected to an S-carboxy-methylation reaction at room temperature for one hour by the addition of 9.5 g of iodoacetic acid to 450 mL of the aqueous keratin solution. The pH value of the aqueous keratin solution was adjusted to 8.5 by the addition of 5N-KOH aqueous solution to give an aqueous solution of S-carboxymethyl keratin solution. This aqueous solution was poured into a dialysis membrane of cellulose and both ends of the membrane were tied up with sewing yarns. The aqueous solution was then dialyzed against pure water for 2 days.

EXAMPLE 16

Weight-Average Molecular Weight of *Bombyx mori* Silk Fibroin Membrane and *Bombyx mori* Silk Fiber A *Bombyx mori* silk fibroin membrane and *Bombyx mori* silk fibers were enzymatically decomposed, sufficiently washed with water and then dried. The resulting sample was subjected to HPLC measurements to determine the weight-average molecular weight thereof. The results thus obtained are listed in the following Table 9.

TABLE 9

| Sample | Enzyme (Concn: mg/mL) | Weight-Average Molecular Weight (kD) Processing Time (hr.) | | | | |
|---|---|---|---|---|---|---|
| | | 0 | 72 | 240 | 408 | 576 |
| *Bombyx mori* Silk Fibroin Membrane | Collagenase (0.2) | 119.8 | 98.5 | 96.8 | 94.3 | — |
| | Chymotrypsin (0.2) | 119.8 | 77.4 | 65.7 | 53.7 | — |
| | Protease (0.2) | 119.8 | 109.6 | 105.6 | 102.4 | — |
| *Bombyx mori* Silk Fiber | Collagenase (0.2) | 233.1 | 184.3 | — | — | 204.4 |
| | Protease (0.2) | 233.1 | 256.5 | — | — | 247.4 |
| | Protease (0.5) | 233.1 | 261.7 | — | — | 241.7 |

In Table 9, each numerical value given in parentheses appearing in the column entitled "Enzyme" means the concentration of an enzyme used. The numerical value "0.2" means that the culture medium contains 0.2 mg of the enzyme per 1 mL of the medium.

As will be clear from the data listed in Table 9, the molecular weight of the *Bombyx mori* silk fibroin membrane was found to be gradually reduced from its initial value of 120,000 D after the proteolytic reaction with the enzyme. More specifically, it was confirmed that the weight-average molecular weight of the membrane was reduced to about 94,000 D and 100,000 D after 408 hours from the initiation of the biodegradation with collagenase and protease, respectively and that the weight average molecular weight of the membrane was rapidly reduced from its initial value of 120,000 D to about 54,000 D at the same biodegradation time. The molecular weight of the untreated *Bombyx mori* silk fiber is about 230,000 D. In this respect, it was found that the weight-average molecular weight thereof was only slightly reduced even after the enzymatic digestion.

EXAMPLE 17

Changes in Weight-average Molecular Weight Associated with Biodegradation Treatment After hydrolyzing the *Bombyx mori* silk fibroin membrane prepared according to the same procedures used in Example 1 with three kinds of enzymes, collagenase, chymotrypsin and protease, for a predetermined period of time (72, 240 or 408 hours), the membrane was sufficiently washed with water to give a sample. Each sample obtained after the biodegradation over a predetermined time was evaluated for the weight-average molecular weight and peak molecular weight. In this respect, the weight-average molecular weight thereof was determined by the high performance liquid chromatography (HPLC) technique. The results thus obtained are summarized in the following Table 10.

TABLE 10

| Enzyme | Weight-Average Molecular Weight (kD) | Peak Molecular Weight (kD) |
|---|---|---|
| Control | 119.8 | 79.8 |
| Collagenase: 0.2 mg/mL | | |
| (72 hrs.) | 98.5 | 53.9 |
| (240 hrs.) | 96.8 | 52.9 |
| (408 hrs.) | 94.3 | 45.8 |
| Chymotrypsin: 0.2 mg/mL | | |
| (72 hrs.) | 77.4 | 41.1 |
| (240 hrs.) | 65.7 | 37.6 |
| (408 hrs.) | 53.7 | 34.8 |
| Protease: 0.2 mg/mL | | |
| (72 hrs.) | 109.6 | 36.4 |
| (240 hrs.) | 105.6 | 33.4 |
| (408 hrs.) | 102.4 | 31.4 |

In Table 10, the time given in parentheses appearing in the column entitled "Enzyme" means the elapsed biodegradation time.

The data listed in Table 10 clearly indicate that when an enzyme digests on the Bombyx mori silk fibroin membrane, the weight-average molecular weight of the membrane is reduced from the initial level of 120,000 D with the progress of the biodegradation time, but after 72 hours from the initiation of the biodegradation, the rate of the molecular weight change of the membrane was reduced. In particular, in the case of collagenase and chymotrypsin, the weight-average molecular weight and the peak molecular weight were reduced with the progress of the biodegradation time. On the other hand, in the case of protease, the weight-average molecular weight was reduced with the progress of the biodegradation time, but the extent of the molecular weight reduction was insignificant and the peak molecular weight was reduced to an extent almost identical to that observed for the chymotrypsin.

COMPARATIVE EXAMPLE 1

Molecular Weight Change of Bombyx mori Silk Fiber Associated with Biodegradation Treatment The changes in the molecular weight of a Bombyx mori silk fiber sample with the elapsed biodegradation time when digesting the silk fiber with collagenase, chymotrypsin and protease were monitored and evaluated by the high performance liquid chromatography technique. The results thus obtained are listed in the following Table 11.

TABLE 11

| Enzyme | Weight-Average Molecular Weight (kD) | Peak Molecular Weight (kD) |
|---|---|---|
| Control | 233.1 | 179.3 |
| Collagenase: 0.2 mg/mL | | |
| (72 hrs.) | 184.3 | 93.7 |
| (576 hrs.) | 204.4 | 109.7 |
| Chymotrypsin: 0.2 mg/mL | | |
| (72 hrs.) | 129.4 | 66.0 |
| (576 hrs.) | 174.4 | 92.8 |
| Protease: 0.2 mg/mL | | |
| (72 hrs.) | 256.5 | 176.9 |
| (576 hrs.) | 247.4 | 155.2 |
| Protease: 0.5 mg/mL | | |
| (72 hrs.) | 261.7 | 173.5 |
| (576 hrs.) | 241.7 | 148.7 |

In Table 11, the time given in parentheses appearing in the column entitled "Enzyme" means the elapsed biodegradation time.

The data listed in Table 11 clearly indicates that the Bombyx mori silk fiber hardly causes any reduction of the weight-average molecular weight and the peak molecular weight even when an enzyme acts on the thread, as compared with the Bombyx mori silk fibroin membrane (Example 17). For this reason, the silk fiber is not useful in the fields wherein biodegradability is required. Materials excellent in biodegradability are, for instance, Bombyx mori silk fibroin membranes and Antheraea pernyi silk fibroin membranes.

EXAMPLE 18

Biodegradation Rate

The following samples were digested for the biodegradation rate observed when these samples were hydrolyzed with protease, collagenase or chymotrypsin: the Bombyx mori silk fiber and the Antheraea pernyi silk fiber; the Bombyx mori silk fibroin membrane (BF membrane) prepared according to the procedures used in Example 1; the Antheraea pernyi silk fibroin membrane (TF membrane) prepared according to the procedures used in Example 2; the hybrid membrane (BF+TF membrane) consisting of Bombyx mori silk fibroin/Antheraea pernyi silk fibroin prepared according to the procedures used in Example 3; the hybrid membrane (BF+Cell membrane) consisting of Bombyx mori silk fibroin/cellulose prepared according to the procedures used in Example 4; and the hybrid membrane (BF+CMK membrane) consisting of Bombyx mori silk fibroin/carboxymethyl chitin prepared according to the method described above. The results thus obtained are summarized in the following Table 12. In this connection, the term "biodegradation rate" is herein defined to be a value obtained by dividing the sample weight observed after 50 hours from the initiation of the biodegradation by the original sample weight (the sample weight prior to the biodegradation) and expressed in terms of "%". Accordingly, when a sample is not biodegraded at all, the biodegradation rate of the sample corresponds to 0%/50 hours.

TABLE 12

| Sample | Enzyme | Enzyme Concn. (mg/mL) | Biodegradation Rate (%/50 hrs.) |
|---|---|---|---|
| Bombyx mori Silk fiber | Protease | 0.2 | 1.4 |
| " | " | 0.4 | 0 |
| Bombyx mori Silk fiber | Collagenase | 0.2 | 0 |
| " | " | 0.5 | 0.5 |
| Bombyx mori Silk fiber | Chymotrypsin | 0.2 | 0.5 |
| " | " | 0.5 | 1.0 |
| Antheraea pernyi Silk fiber | Protease | 0.2 | 0 |
| " | " | 0.5 | 0 |
| Antheraea pernyi Silk fiber | Collagenase | 0.2 | 0 |
| " | " | 0.5 | 0 |
| Antheraea pernyi Silk fiber | Chymotrypsin | 0.2 | 0 |
| " | " | 0.5 | 0 |

TABLE 12-continued

| Sample | Enzyme | Enzyme Concn. (mg/mL) | Biodegradation Rate (%/50 hrs.) |
|---|---|---|---|
| BF Membrane | Protease | 0.2 | 18.2 |
| " | " | 0.5 | 27.3 |
| BF Membrane | Collagenase | 0.2 | 2.0 |
| " | " | 0.5 | 2.2 |
| BF Membrane | Chymotrypsin | 0.5 | 9.1 |
| TF Membrane | Protease | 0.2 | 3.1 |
| " | " | 0.5 | 11.2 |
| TF Membrane | Chymotrypsin | 0.2 | 14.5 |
| BF:TF (10:0) | Protease | 0.2 | 18.2 |
| BF:TF (8:2) | " | 0.2 | 15 |
| BF:TF (6:4) | " | 0.2 | 15 |
| BF:TF (4:6) | " | 0.2 | 0 |
| BF:TF (2:8) | " | 0.2 | 0 |
| BF:TF (0:10) | " | 0.2 | 3.1 |
| BF:Cell (10:0) | Protease | 0.2 | 18.2 |
| BF:Cell (8:2) | " | 02 | 13.6 |
| BF:Cell (6:4) | " | 0.2 | 22.7 |
| BF:Cell (4:6) | " | 0.2 | 21.4 |
| BF:Cell (2:8) | " | 0.2 | 5.9 |
| BF:Cell (0:10) | " | 0.2 | 2.5 |
| BF:CMK (6:4) | Protease | 0.2 | 12.1 |
| BF:CMK (2:8) | " | 0.2 | 8.5 |

In Table 12, "BF:TF" and "BF:Cell" represent the hybrid membrane of *Bombyx mori* silk fibroin (BF) and *Antheraea pernyi* silk fibroin (TF) and the hybrid membrane of *Bombyx mori* silk fibroin (BF) and cellulose (Cell), respectively and the corresponding numerical values given in parentheses mean that the mixing ratios of BF to TF and those of BF to Cell are 100/0, 80/20, 60/40, 40/60, 20/80 and 0/100.

The data listed in Table 12 also clearly indicates that when digesting a hybrid membrane of *Bombyx mori* silk fibroin and *Antheraea pernyi* silk fibroin with protease, the hybrid membrane containing *Antheraea pernyi* silk fibroin in an amount ranging from 60 to 80% does not substantially undergo any biodegradation from the viewpoint of the biodegradation rate and this is substantially consistent with the conclusion deduced from the data concerning the rate of residual sample weight discussed in Example 13. This is a property, which is never observed for the membrane simply consisting of *Bombyx mori* silk fibroin or *Antheraea pernyi* silk fibroin.

EXAMPLE 19

Composite Materials having Different Shapes

A mixture of an aqueous solution of *Bombyx mori* silk fibroin and an aqueous solution of *Antheraea pernyi* silk fibroin was poured into a beaker. A dilute aqueous acetic acid solution was gradually added to the mixed aqueous solution in small portions to control the pH value of the whole aqueous solution to 2.5 and to form a gel-like product of *Bombyx mori* silk fibroin and *Antheraea pernyi* silk fibroin. Moreover, the gel-like product obtained was directly subjected to lyophilization without removing any moisture from the product according to a known method to prepare a porous product of *Bombyx mori* silk fibroin and *Antheraea pernyi* silk fibroin.

Alternatively, a mixture of an aqueous solution of *Bombyx mori* silk fibroin and an aqueous solution of *Antheraea pernyi* silk fibroin was cast dried on a polyethylene substrate to give a transparent composite membrane.

Moreover, acetic acid was added to a mixture of an aqueous solution of *Bombyx mori* silk fibroin and an aqueous solution of *Antheraea pernyi* silk fibroin, followed by the control of the pH value thereof to 3.0 and the lyophilization of the aqueous mixture by a known method to form a powdery hybrid consisting of *Bombyx mori* silk fibroin and *Antheraea pernyi* silk fibroin.

EXAMPLE 20

Amino Acid Analysis

A *Bombyx mori* silk fibroin membrane was digested with protease and then the biodegraded sample was subjected to amino acid analysis to examine the relationship between the results of the amino acid analysis and the biodegradation time. The results thus obtained are summarized in the following Table 13. In Table 13, the amount of each amino acid residue is expressed in terms of "mole %".

TABLE 13

| Amino Acid | Biodegradation Time (day) | | | |
|---|---|---|---|---|
| | 0 | 3 | 10 | 17 |
| Cyst | 0.03 | 0.04 | 0.02 | 0.00 |
| Asp | 1.28 | 0.58 | 0.83 | 0.59 |
| Glu | 1.09 | 0.54 | 0.77 | 0.51 |
| Ser | 10.89 | 9.96 | 10.47 | 10.68 |
| Gly | 45.00 | 46.49 | 45.95 | 46.73 |
| His | 0.15 | 0.10 | 0.10 | 0.10 |
| Arg | 0.48 | 0.32 | 0.36 | 0.29 |
| Thr | 0.78 | 0.50 | 0.59 | 0.54 |
| Ala | 29.43 | 31.52 | 30.36 | 31.71 |
| Pro | 0.35 | 0.27 | 0.28 | 0.26 |
| Tyr | 5.76 | 5.74 | 5.80 | 5.05 |
| Val | 2.31 | 2.17 | 2.24 | 1.85 |
| Met | 0.09 | 0.07 | 0.06 | 0.27 |
| Cyst | 0.02 | 0.00 | 0.00 | 0.00 |
| Ile | 0.66 | 0.46 | 0.59 | 0.41 |
| Leu | 0.51 | 0.31 | 0.53 | 0.28 |
| Phe | 0.81 | 0.71 | 0.77 | 0.56 |
| Lys | 0.36 | 0.22 | 0.28 | 0.17 |
| Total | 100.00 | 100.00 | 100.00 | 100.00 |
| Gly | 45.00 | 45.95 | 46.49 | 46.73 |
| Ala | 29.43 | 30.36 | 31.52 | 31.71 |
| Ser | 10.89 | 10.47 | 9.96 | 10.68 |
| Total-1 | 85.32 | 86.78 | 87.97 | 89.12 |
| Tyr | 5.76 | 5.80 | 5.74 | 5.05 |
| Acid | 2.40 | 1.62 | 1.16 | 1.10 |
| Basic | 0.99 | 0.74 | 0.64 | 0.56 |
| Others | 5.53 | 5.06 | 4.49 | 4.18 |
| Total-2 | 14.68 | 13.22 | 12.03 | 10.88 |

In Table 13, "Total" means the amount of the whole amino acids residues obtained in the amino acid analysis expressed in the unit of mole %, "Total-1" means the total amount of the amino acid residues or Gly, Ala and Ser constituting the crystalline region, while "Total-2" means the total amount of acidic amino acid residues (acid) such as Glu and Asp, basic amino acid residues (basic), such as Lys, Arg and His, as well as other amino acids.

As will be seen from the results listed in Table 13, there is observed a distinct tendency in the results obtained by the amino acid analysis of the biodegraded *Bombyx mori* silk fibroin membrane. More specifically, the total amount of Gly, Ala and Ser, which are principal amino acids constituting the crystalline region of the silk fibroin, gradually increases with the lapse of the digestion time. Meanwhile, the total amount of bulky polar side chain-containing amino acids, such as Tyr, acidic amino acids and basic amino acids is reduced. In other words, the amino acid composition of the silk fibroin is shifted to that observed for the crystalline region as the biodegradation proceeds, as described above. Therefore, it would be considered that when an enzyme acts on silk fibroin, the enzyme first acts on the amorphous region susceptible to the enzymatic attack to induce the digestion of the fibroin. The crystalline region of the fibroin almost susceptible to the attack of the enzyme remains even after the biodegradation. Accordingly, the principal chemical structure of the fibroin is shifted to mainly comprising crystalline amino acids as the biodegradation proceeds.

EXAMPLE 21

Adsorption of Metal Ions

Experiments were conducted according to the method for adsorbing metal ions, as described above. The metal salt aqueous solutions used herein were a 0.5 mM aqueous solution of silver nitrate ($AgNO_3$) and a 0.5 mM aqueous solution of copper nitrate ($Cu(NO_3)_2$). In each of these aqueous solutions, a Bombyx mori silk fibroin membrane (BF membrane) prepared according to the same procedures used in Example 1, an Antheraea pernyi silk fibroin membrane (TF membrane) prepared according to the same procedures used in Example 2 and composite membranes (80:20 and 50:50 (weight ratio) BF+TF membranes) consisting of Bombyx mori silk fibroin and Antheraea pernyi silk fibroin prepared according to the same procedures used in Example 3, were immersed at a temperature of 25° C. for 30 minutes to adsorb silver ions or copper ions on each sample and to thus determine the quantity of metal ions adsorbed on each sample.

Moreover, various kinds of biodegradable biopolymer membranes on which silver ions had been adsorbed according to the foregoing method were evaluated for the antibacterial activity against tomato canker causal bacterium: Corynebacterium michiganense pv. michiganense.

The amount of the metal ion adsorption and the antibacterial activity thus obtained are listed in the following Table 14.

TABLE 14

| Sample | Amt. of $Ag^+$ (mmol/g) | Amt. of $Cu^{2+}$ (mmol/g) | Antibacterial Activity (mm) |
|---|---|---|---|
| BF | 0.18 | 0.23 | 2 |
| TF | 0.24 | 0.30 | 2.5 |
| BF + TF (80:20) | 0.72 | 0.95 | 8 |
| BF + TF (50:50) | 0.93 | 1.25 | 8.7 |

The data listed in Table 14 clearly indicates that the composite membrane obtained by combining Bombyx mori silk fibroin and Antheraea pernyi silk fibroin may absorb metal ions in an amount greater than that observed for the membrane simply consisting of Bombyx mori silk fibroin or Antheraea pernyi silk fibroin. As a result, the former displays antibacterial activity toward plant pathogenic fungi or bacteria. Thus, the silk fibroin-containing composite material can be used as a metal adsorbent and an antibacterial material.

EXAMPLE 22

Rate of Light Transmission of Silk Protein Membrane

A Bombyx mori silk fibroin membrane (BF membrane), an Antheraea pernyi silk fibroin membrane (TF membrane) and composite membranes (80:20 and 50:50 (weight ratio) BF+TF membranes) obtained by hybridizing Bombyx mori silk fibroin and Antheraea pernyi silk fibroin were evaluated for the transmittance spectra using a self-recording (or autographic) spectrophotometer (Model: W-2100S) available from Shimadzu Corporation. In this connection, the spectra determined were transmittance spectra, including those originated from surface reflection. The resulting rates of light transmission are listed in the following Table 15.

TABLE 15

| Sample | Rate of Light Transmission (%) |
|---|---|
| BF Membrane | 87.3 |
| TF Membrane | 84.7 |
| BF:TF (80:20) Membrane | 93.4 |
| BF:TF (50:50) Membrane | 90.1 |

The data listed in Table 15 clearly indicates that the composite membrane is highly permeable to light rays as compared with the membrane simply consisting of Bombyx mori silk fibroin or Antheraea pernyi silk fibroin or the former has a degree of clearness higher than that observed for the latter.

EXAMPLE 23

Drug-sustained Release Properties

To an equivalent mixture of a 2% aqueous solution of Bombyx mori silk fibroin and a 2% aqueous solution of Antheraea pernyi silk fibroin prepared according to the same procedures used in Example 3, there was gently added an aqueous solution prepared by dissolving 5 mg of acetyl salicylic acid in 50 mL of water. The aqueous mixed solution allowed to stand at room temperature was gradually converted into a gel. The resulting gel was once frozen at a temperature of −10° C. and then dried in vacuo to form a porous composite material containing acetyl salicylic acid. The porous composite material was digested in an enzyme solution containing 2 mg/mL of protease over a predetermined period of time (24 and 72 hours). The amount of the agent gradually released from the porous composite material during the digestion process was evaluated on the basis of the UV absorbance at 206.9 nm, which was determined using a UV absorbance meter available from Shimadzu Corporation. The results thus obtained are listed in the following Table 16. Each UV absorbance value listed in Table 16 is obtained by subtracting the UV absorption observed for the initial enzyme solution or observed at the biodegradation time of 0 from the UV absorption observed for the enzyme solution containing the agent gradually released from the porous composite material.

Moreover, as a control, a porous material simply consisting of Bombyx mori silk fibroin (BF) or Antheraea pernyi silk fibroin (TF) was evaluated for the sustained release characteristics according to the same procedures used above in connection with the foregoing porous composite material. The results are summarized in the following Table 16.

TABLE 16

| | Biodegradation Time (hr.) | | |
|---|---|---|---|
| Sample | 0 | 24 | 72 |
| BF Porous Material | 0.10 | 0.259 | 0.259 |
| TF Porous Material | 0.10 | 0.270 | 0.271 |
| Porous Composite Material | 0.10 | 0.265 | 0.293 |

The data listed in Table 16 clearly indicates that the porous composite material containing acetyl salicylic acid gradually releases the drug over a long period of time, as compared with the drug-release behavior of the porous material simply consisting of *Bombyx mori* silk fibroin or *Antheraea pernyi* silk fibroin. This clearly indicates that the composite membrane possesses drug-sustained release characteristics.

EXAMPLE 24

FT-IR of Composite Membrane

The following membranes were subjected to the FT-IR measurements: a *Bombyx mori* silk fibroin membrane (BF membrane) prepared according to the procedures used in Example 1; an *Antheraea pernyi* silk fibroin membrane (TF membrane) prepared according to the procedures used in Example 2; a composite membrane (BF+TF membrane) consisting of *Bombyx mori* silk fibroin and *Antheraea pernyi* silk fibroin prepared according to the procedures used in Example 3; a composite membrane (BF+CMK membrane) consisting of *Bombyx mori* silk fibroin and carboxymethyl chitin used in Example 18; a composite membrane (TF+CMK membrane) consisting of *Antheraea pernyi* silk fibroin and carboxymethyl chitin; a membrane consisting of CMK alone; and a composite membrane (BF+PVA membrane) consisting of *Bombyx mori* silk fibroin and polyvinyl alcohol, to determine wave numbers appearing within the range of from 2000 to 500 $cm^{-1}$. The results thus obtained are summarized in the following Table 17.

TABLE 17

| Sample | Wave Number ($cm^{-1}$) and Absorption Intensity |
| --- | --- |
| BF Membrane | 1654, 1539, 1455, 1414, 1383, 1334, 1240, 1170, 1071, 1061, 1016, 950, 670, 532 |
| TF Membrane | 1650, 1546, 1274, 615 |
| BF + TF Membrane | 1654, 1650, 1274, 950, 670, 615, 533 |
| BF + CMK | 1654, 1542, 1528, 1451, 1412, 1381, 1333, 1242, 1162, 1109, 1070, 949, 666, 559 |
| TF + CMK (2:8) Membrane | 1657, 1548, 1451, 1378, 1316, 1156, 1113, 1069, 1037, 951, 900, 618, 526 |
| TF + CMK (8:2) Membrane | 1653, 1542, 1282, 1334, 1307, 659, 617, 525 |
| CMK Membrane | 1654, 1592, 1570, 1413, 1374, 1318, 1155, 1111, 1071, 1038, 946, 901, 685, 615, 571 |
| BF + PVA (2:8) Membrane | 1420-1440, 1326, 1232, 1093, 913, 849 |

In Table 17, the term "TF+CMK (2:8)" means a composite membrane prepared by blending *Antheraea pernyi* silk fibroin and carboxymethyl chitin in a weight ratio of 20:80. In addition, the term "BF+PVA (2:8)" means a composite membrane prepared by blending *Bombyx mori* silk fibroin and polyvinyl alcohol in a weight ratio of 20:80.

The data listed in Table 17 indicates that the IR spectra observed for the composite materials consisting of *Bombyx mori* silk fibroin and secondary substances, and the composite materials consisting of wild silkworm silk fibroin and secondary substances, include only spectra ascribable to two kinds of constituents, which are superimposed to one another and are free of any spectrum other than those ascribable to the two constituents. This clearly indicates or suggests that any new linkage is not formed between the *Bombyx mori* silk fibroin or the wild silkworm silk fibroin and the secondary substance.

The foregoing indicates that in the composite materials consisting of domesticated or wild silkworm silk fibroin and secondary substances selected from the group consisting of cellulose, chitin, chitosan, chitosan derivatives, wool keratin and polyvinyl alcohol, there is no chemical or covalent bond between the domesticated or wild silkworm silk fibroin and the secondary substance, but that these two components are simply coagulated through the action of hydrogen bonds formed in between. This is because the composite material is simply prepared, by casting a mixture of aqueous solutions of respective constituents on the surface of a substrate and then solidification through evaporation to dryness, without using any particular agent for cross-linking molecules. In this connection, the aqueous mixture is allowed to stand and, if desired, gently stirred so as not to cause any coagulation of these two kinds of molecules or solidification due to any abrupt mixing mechanical operation prior to the casting on the substrate surface.

As discussed above in detail, the biodegradable biopolymer material of the present invention comprises an insect's biopolymer alone, such as domesticated silkworm silk fibroin or wild silkworm silk fibroin, or a composite material comprising domesticated or wild silkworm silk fibroin and a secondary substance or at least one compound selected from the group consisting of cellulose, wool keratin, chitin, chitosan, chitosan derivatives and polyvinyl alcohol, and the biodegradation of these materials may be controlled.

The biodegradable biopolymer material of the present invention should be insolibilized in water prior to the biodegradation experiments, but it is also possible to use any conventionally known agent for cross-linking protein molecules, such as formaldehyde or epoxy compounds. In addition, the silk protein membrane or the composite material may be insolibilized in water by simple treatments, for instance, by lightly immersing the membrane in an aqueous alcohol solution, such as an aqueous methanol or ethanol solution, and then drying at room temperature.

The susceptibility of a hybrid to biodegradation may be determined by the degree of insolibilization of a domesticated or wild silkworm silk fibroin membrane, the choice of the secondary substance, the mixing ratio of the domesticated or wild silkworm silk fibroin to the secondary substance, the kind of enzyme selected, the enzyme concentration used and the processing time. Therefore, a hybrid having a desired biodegradability can be prepared by appropriately selecting the conditions for producing the same, the mixing ratio of the constituents and/or the conditions for biodegradation.

The composite material made of domesticated or wild silkworm silk fibroin with secondary substances would permit the achievement of such a significant effect that the surface of the resulting blending shows excellent biochemical characteristics, which are never observed for the surface of the membrane comprising domesticated or wild silkworm silk fibroin alone, or the secondary substance alone. For instance, the surface of the hybrid is excellent in the rate of biological cell-growth as compared with the surface of the membrane comprising the domesticated silkworm silk fibroin alone or the secondary substance alone. In addition, the hybrid is also excellent in the ability of coating the surface of general organic polymers, such as PET, and the use of a hybrid material would permit the improvement of the resistance of a membrane to mechanical friction.

If a useful substance, such as a water-soluble medicine or a pharmacological component, is included in the biodegradable biopolymer material of the present invention, the medicine or the pharmacological component can gradually be released while biodegrading the biodegradable biopolymer material in the living body. Therefore, the material can be used as a sustained release material.

The biodegradability can be reduced by the use of the silk fibroin fibers from domesticated or wild silkworms. If an easily biodegradable material is desired, a membrane-like material may be used. Such a membrane may be prepared by dissolving domesticated or wild silkworm silk fibers in a neutral salt solution, desalting the resulting solution using a dialysis membrane of cellulose and then solidifying the resulting aqueous solution through drying. The domesticated silkworm silk fibroin membrane can easily be biodegraded, as compared with the wild silkworm silk fibroin membrane. Therefore, a hardly biodegradable composite material comprising domesticated and wild silkworm silk fibroins may be obtained by increasing the content of the wild silkworm silk fibroin present in the composite material.

When the biodegradable biopolymer material of the present invention is used while it is embedded in the living body, the material is ultimately decomposed into lower molecules, such as water and carbon dioxide, by the action of enzymes present in the body, such as protease, and then is excreted outside the body. The easily biodegradable domesticated silkworm silk fibroin membrane may be biodegraded within a relatively short period of time even when it is embedded in the body unlike the hardly biodegradable domesticated silkworm silk fibroin fibers. Therefore, the membrane can be used for temporarily helping the repairable damaged biological tissues in their healing or for the preparation of a sustained release drugs, as discussed above. The absorptive material of the present invention may be used in a variety of applications, such as the suture of incised and/or wound portions, arrest of hemorrhage, bone fixation, a clue for tissue-regeneration and a means for preventing adhesion.

The biodegradable biopolymer material of the present invention is digested and deteriorated through digestion with a protease. Therefore, it may also be used as a sustained release carrier for a useful substance, such as a medicine or a physiologically active substance. For instance, when embedding, in the biodegradable biopolymer material, a product obtained by taking the useful substance in the biopolymer material or by fixing the useful substance to the biopolymer material, the useful substance is gradually released within the living body, while the biopolymer material is digested with enzymes present in the body.

Cellulose derivatives have been effectively utilized in various fields, such as food additives, cosmetics, additives for medicines and medicines, such as an antithrombotic agent. Therefore, the composite material consisting of domesticated silkworm silk fibroin and cellulose may be used in fields identical to those listed above in connection with cellulose. Moreover, the hybridization of domesticated silkworm silk fibroin with cellulose would permit the mechanical properties of the silk fibroin, in particular, in its dried conditions. In addition, the hybridization of domesticated or wild silkworm silk fibroin with a secondary substance, such as cellulose, would permit the production of a material having improved moldability and transparency, as well as cell adhesion properties, as compared with those observed for a membrane simply consisting of domesticated or wild silkworm silk fibroin.

The domesticated silkworm silk fibroin membrane may be relatively easily biodegraded with protease. For this reason, if hybridizing the domesticated silkworm silk fibroin with hardly biodegradable wild silkworm silk fibroin, the resulting hybrid membrane would have a controlled degree of biodegradation and may have an improved film-forming ability and enhanced transparency.

The extent of biodegradation of the biodegradable biopolymer membrane according to the present invention can be controlled by a simple treatment. Moreover, in a hybrid material, the biodegradable biopolymer moiety is firmly adhered to the surface of a secondary substance, the hybrid material is excellent in the wear resistance. Therefore, the substrate coated with a hybrid material is improved in the biological cell-growth properties on the surface thereof, as compared with substrate coated only with a protein. Accordingly, the hybrid material is useful as a cell-growth substrate capable of being used in the field of biotechnology.

When immersing the biodegradable biopolymer material of the present invention in an aqueous solution containing antibacterial metal ions, a large amount of such metal ions are adsorbed on the biopolymer material. Therefore, the biopolymer material carrying such metal ions adsorbed thereon is useful as an antibacterial fiber material. Moreover, when immersing the biopolymer material in waste water, it can adsorb metal ions present in the waste water. Accordingly, the biopolymer material is also effective as a fibrous material for adsorbing metal ions in waste water.

The biodegradable biopolymer material of the present invention possesses water-absorbing properties, which make the material applicable as a water-absorbable resin used in, for instance, disposable hygienic goods and household goods, water cut-off agents, soil conditioners, dewing inhibitors, and water-retention agents for agriculture and horticulture. The present invention would also permit the supply of a water-absorbing material having such biodegradability for a low price without requiring any complicated steps. For this reason, the material of the present invention can be applied to any fields of applications identical to those for the conventionally known water-absorbing resins. For instance, the material of the present invention can be used in a wide variety of fields, such as hygiene (typically use as a diaper and a sanitary good), medical services (for instance, use in cataplasms), civil engineering and architecture (for instance, use as an agent for coagulating sludge), foods, industries, and agriculture and horticulture (for instance, use as a soil conditioner and a water-retention agent).

The invention claimed is:

1. A biodegradable biopolymer material comprising a composite material comprising silk fibroin from wild silkworm and keratin from wool, wherein the keratin from wool is reduced keratin or S-carboxymethyl keratin.

2. The biodegradable biopolymer material of claim 1, wherein the biodegradable biopolymer material has a shape that is selected from the group consisting of sheet-like, membrane-like, powdery, bead-like, gel-like, fibrous, tubular, and hollow thread-like.

3. A metal ion-adsorbing material comprising a biodegradable biopolymer material that comprises:
    a composite material comprising silk fibroin from wild silkworm and keratin from wool,
    wherein the keratin from wool is reduced keratin or S-carboxymethyl keratin.

4. The metal ion-adsorbing material as set forth in claim 3, wherein the metal ions are antibacterial metal ions or metal ions present in waste water.

5. A sustained release carrier for a useful substance comprising a biodegradable biopolymer material that comprises:
    a composite material comprising silk fibroin from wild silkworm and keratin from wool,
    wherein the keratin from wool is reduced keratin or S-carboxymethyl keratin.

6. The sustained release carrier for a useful substance as set forth in claim 5, wherein the biodegradable biopolymer material is a porous substance.

7. A substrate for growth of biological cells comprising a composite material comprising silk fibroin from wild silkworm and keratin from wool, wherein the substrate is used for the growth of biological cells, and wherein the keratin from wool is reduced keratin or S-carboxymethyl keratin.

8. A method for the preparation of a membrane-like biodegradable polymer material comprising silk fibroin from a wild silkworm and keratin from wool, wherein the keratin is reduced keratin or S-carboxymethyl keratin, comprising the steps of:
  (a) applying, onto the surface of a substrate, an aqueous mixed solution comprising an aqueous solution of silk fibroin from a wild silkworm and an aqueous solution of keratin from wool, wherein the keratin from wool is reduced keratin or S-carboxymethyl keratin, and
  (b) cast drying the applied solution to form the membrane-like biodegradable biopolymer material, wherein the aqueous mixed solution is prepared by uniformly admixing the constituents of the aqueous mixed solution by stirring them such that they do not undergo any gelation, precipitation and/or coagulation reaction.

9. A method for the preparation of a powdery biodegradable biopolymer material comprising silk fibroin from a wild silkworm and keratin from wool, wherein the keratin is reduced keratin or S-carboxymethyl keratin, comprising the steps of:
  (a) freezing an aqueous mixed solution comprising an aqueous solution of silk fibroin from wild silkworm and an aqueous solution of keratin from wool, wherein the keratin from wool is reduced keratin or S-carboxymethyl keratin, and wherein the aqueous mixed solution is prepared by uniformly admixing the constituents of the mixed aqueous solution by stirring them such that they do not undergo any gelation, precipitation and/or coagulation reaction, and
  (b) drying the frozen aqueous solution under a reduced pressure to form the powdery biodegradable biopolymer material.

10. A method for the preparation of a gel-like biodegradable biopolymer material comprising silk fibroin from a wild silkworm and keratin from wool, wherein the keratin is reduced keratin or S-carboxymethyl keratin, comprising the steps of:
  (a) adjusting the pH value of an aqueous mixed solution comprising an aqueous solution of silk fibroin from wild silkworm and an aqueous solution of keratin from wool, wherein the keratin is reduced keratin or S-carboxymethyl keratin, to a pH level within the acidic pH range, and
  (b) entirely coagulating the aqueous mixed solution to give the gel-like biodegradable biopolymer material.

11. A method for the preparation of a porous body, comprising the step of subjecting the gel-like biodegradable biopolymer material prepared according to the method set forth in claim 10 to lyophilization to obtain the porous body.

12. The method as set forth in claim 8, wherein the concentrations of the aqueous solution of the silk fibroin from wild silkworm and the aqueous solution of the keratin from wool used in the preparation of the mixed aqueous solution range from 0.1 to 5% w/v, respectively.

13. The method as set forth in claim 9, wherein the concentrations of the aqueous solution of the silk fibroin from wild silkworm and the aqueous solution of the keratin from wool used in the preparation of the mixed aqueous solution range from 0.1 to 5% w/v, respectively.

14. The method as set forth in claim 10, wherein the concentrations of the aqueous solution of the silk fibroin from wild silkworm and the aqueous solution of the keratin from wool used in the preparation of the mixed aqueous solution range from 0.1 to 5% w/v, respectively.

15. The method as set forth in claim 11, wherein the concentrations of the aqueous solution of the silk fibroin from wild silkworm and the aqueous solution of the keratin from wool used in the preparation of the mixed aqueous solution range from 0.1 to 5% w/v, respectively.

* * * * *